(12) United States Patent
Chong et al.

(10) Patent No.: US 7,018,637 B2
(45) Date of Patent: Mar. 28, 2006

(54) MULTI-OLIGOSACCHARIDE GLYCOCONJUGATE BACTERIAL MENINGITIS VACCINES

(75) Inventors: Pele Chong, Richmond Hill (CA); Alf Lindberg, Lyons (FR); Michel Klein, Willowdale (CA)

(73) Assignee: Aventis Pasteur, Inc, Swiftwater, PA (US)

( * ) Notice: Subject to any disclaimer, the term of this patent is extended or adjusted under 35 U.S.C. 154(b) by 0 days.

(21) Appl. No.: 09/027,956

(22) Filed: Feb. 23, 1998

(65) Prior Publication Data

US 2001/0048929 A1 Dec. 6, 2001

(51) Int. Cl.
*A61K 39/385* (2006.01)
*A61K 39/00* (2006.01)
*A61K 39/095* (2006.01)
*C07K 1/00* (2006.01)
*C07K 14/00* (2006.01)

(52) U.S. Cl. .............................. 424/197.11; 424/184.1; 424/277.1; 424/193.1; 424/194.1; 424/244.1; 424/249.1; 424/250.1; 530/333; 530/350; 530/395; 530/402; 530/807; 530/810

(58) Field of Classification Search ................. 424/93.1, 424/88, 184.1, 277.1, 193.1, 197.11, 244.1, 424/249.1, 250.1, 197.1, 194.1; 530/300, 530/350, 395, 402, 333, 807; 435/7.1
See application file for complete search history.

(56) References Cited

U.S. PATENT DOCUMENTS

| | | | | |
|---|---|---|---|---|
| 5,041,516 A | * | 8/1991 | Frechet et al. ................. 528/44 |
| 5,229,490 A | | 7/1993 | Tam ........................... 530/324 |
| 5,306,492 A | * | 4/1994 | Porro et al. .................... 424/88 |
| 5,370,872 A | * | 12/1994 | Cryz et al. ................ 424/194.1 |
| 5,371,197 A | * | 12/1994 | Marburg et al. ............. 530/404 |
| 5,567,411 A | * | 10/1996 | Keana et al. ................. 424/9.1 |
| 5,585,100 A | * | 12/1996 | Mond et al. .............. 424/193.1 |
| 5,623,057 A | * | 4/1997 | Marburg et al. ............. 530/404 |
| 5,795,580 A | * | 8/1998 | Jennings et al. .......... 424/244.1 |
| 5,807,553 A | * | 9/1998 | Malcolm .................. 424/193.1 |
| 5,843,461 A | * | 12/1998 | Jennings et al. .......... 424/244.1 |
| 5,847,112 A | * | 12/1998 | Kniskern et al. ............ 536/127 |
| 5,882,645 A | * | 3/1999 | Toth et al. ................. 424/194.1 |
| 5,955,079 A | * | 9/1999 | Mond et al. .............. 424/193.1 |
| 5,965,544 A | * | 10/1999 | Renkonen et al. ............. 514/54 |
| 6,180,758 B1 | * | 1/2001 | Chong et al. ................ 530/326 |
| 6,403,306 B1 | * | 6/2002 | Stephens et al. ................ 435/6 |
| 6,420,169 B1 | * | 7/2002 | Read et al. ................. 435/289.1 |
| 6,426,067 B1 | * | 7/2002 | Matthews et al. ......... 424/78.08 |
| 6,482,928 B1 | * | 11/2002 | Pai et al. ................... 530/387.9 |
| 6,540,999 B1 | * | 4/2003 | Harn et al. ............... 424/184.1 |
| 6,656,472 B1 | * | 12/2003 | Chong et al. ............. 424/193.1 |
| 2002/0123609 A1 | * | 9/2002 | Frechet et al. ............... 528/403 |
| 2004/0022840 A1 | * | 2/2004 | Nagy et al. ................. 424/450 |
| 2004/0047866 A1 | * | 3/2004 | Harn et al. ............... 424/184.1 |
| 2004/0057958 A1 | * | 3/2004 | Waggoner et al. ........ 424/184.1 |
| 2004/0096461 A1 | * | 5/2004 | Michon et al. .......... 424/203.1 |

FOREIGN PATENT DOCUMENTS

| | | | |
|---|---|---|---|
| EP | 497525 | * | 8/1992 |
| WO | WO 96/40225 | | 12/1996 |
| WO | WO 96/40242 | * | 12/1996 |
| WO | WO 98/43677 A | | 10/1998 |

OTHER PUBLICATIONS

Chong et al, Infec. Immun., 65(12):4918–25, Dec. 1997.*
Zhang et al, Cancer Res., 55:3364–3368, Aug. 1, 1995.*
Paul, Immunology, Raven Press, 1993.*
Lindberg et al, Infection and Immunity, 1983, 41/3:888–895.*
Robbins et al, Annals NY Acad. Sci., 1995, 754:68–82.*
Chong et al, Infection and Immunity, 1992, 60/11:4640–4647.*
Paton, Trends in Microbiology, 1998, 6/3:85–87.*
Michon et al, Vaccine, 1998, 16/18:1732–1741.*
Wessels et al, J. Infectious Diseases, 1995, 171:879–884.*
Porro et al, Molecular Immunology, 1986, 23/4:385–391.*
Briles et al, Microbial Drug Resistance, 1997, 3/4:401–408.*
Zhang et al, Infection and Immunity, 2001, 69/6:3827–3836.*
Bay S. et al: "Preparation of a Multiple Antigen Glycopeptide (Mag) Carrying the TN Antigen" Journal of Peptide Research, vol. 49, No. 6, Jun. 1, 1997, pp. 620–625.
Steinhoff, M.C. et al: "A Randomized Comparison of Three Bivalent Streptococcus Pneumoniae Glycoprotein Conjugage Vaccines in Young Children: Effect of Polysaccharide Size and Linkage Characteristics", Pediatric Infectious Disease Journal, vol. 13, No. 5, May 1, 1994, pp. 368–372.

(Continued)

*Primary Examiner*—N. M. Minnifield
(74) *Attorney, Agent, or Firm*—Aventis Pasteur, Inc

(57) ABSTRACT

Multivalent immunogenic molecules comprise a carrier molecule containing at least one functional T-cell epitope and multiple different carbohydrate fragments each linker to the carrier molecule and each containing at least one functional B-cell epitope. The carrier molecule inputs enhanced immunogenicity to the multiple carbohydrate fragments. The carbohydrate fragments may be capsular oligosaccharide fragments from *Streptococcus pneumoniae*, which may be serotypes 1, 4, 5, 6B, 9V, 14, 18C, 19F or 23F, or *Neisseria meningitidis*, which may be serotype A, B, C, W-135 or Y. Such oligosaccharide fragments may be sized from 2 to 5 kDa. Alternatively, the carbohydrate fragments may be fragments of carbohydrate-based tumor antigens, such as Globo H, Le$^Y$ or STn. The multivalent molecules may be produced by random conjugation or site-directed conjugation of the carbohydrate fragments to the carrier molecule. The multivalent molecules may be employed in vaccines or in the generation of antibodies for diagnostic application.

15 Claims, 12 Drawing Sheets

OTHER PUBLICATIONS

Malcolm, A.J. "Improved Conjugate Vaccines" Journal of Cellular Biochemistry, Supplement, vol. Suppl. 17C, No. 11, Feb. 8, 1993, p. 90.

Paradiso, P.R. et al: "Glycoconjugate Vaccines: future combinations" Developments in Biological Standardization, (1996) 87 269–275 Ref: 12.

MMWR, (1994) 43:23–26.

MMWR (1989) 38:64–76.

Austrian R. (1981) *Rev. Infect. Dis.* 3 (Suppl):S1–S17.

Dagan et al., (1992) *J. Am. Med. Assoc.* 268:3328–3332).

H. Jennings et al, (1986), J. Immun. 127, 1011.

H. Jennings et al. J. Immunol., 1986, 137, 1708.

Peeters et al., (1991) *Infect. Immun.* 59:3504–3510.

Paradiso et al., (1993) *Vaccine Res.* 4:239–248.

Schneerson et al. (1980) *J. expt. Med.* 152: 361.

Barington et al. 1993, *Infect. Immun.* 61:432–438.

Svennerholm, 1957, *Biochem. Biophys. Acta.* 604:24.

Walker et al. (1987), *Infect. Immun.* 58:1184–1189.

Yother and Briles (1992), *J. Bacteriol.* 174:601–609.

Sampson et al., *Infect. Immun.* 62:319–324.

Rokbi et al., (1995) *FEMS Microbiol. Lett.* 132: 277–283.

Stimson et al., (1995), *Mol. Microbiol.* 17:1201–1214.

McGuinness et al., (1990), *J. Exp. Med.* 171:1871–1882.

De Velasco et al., *Infect. Immun.* 63:961–968.

Eby et al., (1994) In Vaccine 94:*Modern Approaches to Vaccines* pp. 119–124. Edited by E. Norry, F. Brown, R.M. Chanock and Ginsberg, H.S. Cold Spring Harbor, N.Y. Cold Spring Harbor Press.

Kandil et al., (1997) *Glycoconjugate J.* 14:13–17.

Tam (1996, *J. Immun. Meth.* 196:1732).

Ridles et al., (1983) *Methods Enzymol.* 91: 49–60.

Sia et al, Scan. J. Immunol. 26: 683–690 author DY Sia and JL. Chou.

Wiertz et al., In Rivier, J and Marshall, G.R. (Ed.) *Peptides: Chemistry, Structure and Biology,* (Proceedings of the 11th American Peptide Symposium), ESCOM, Leiden, 1990, p. 371–372.

McQueen et al., (1991) *Pediatr. Res.* 31 (part 2): Abstract 1056.

* cited by examiner-

| PN(123–140) | GVRGAVNDLLAKWHQDYGQG | (SER ID NO : 5) |
| PN(263–281) | GFEALIKGVKVAPQTEWKQIG | (SER ID NO : 6) |
| SP37 | GIIAKNIAKQLIAKDPKNKDFYEKNG | (SER ID NO : 7) |

MULTI-OLIGOSACCHARIDE GLYCOCONJUGATE BACTERIAL MENINGITIS VACCINES

FIELD OF INVENTION

The present invention is related to the field of vaccines and is particularly related to the development of novel glycoconjugation technologies which can be used to prepare glycoconjugates in which multi-oligosaccharides are covalently linked to the same carrier protein.

BACKGROUND OF THE INVENTION

*Haemophilus influenzae* type b (Hib), *Neisseria meningitidis* and *Streptococcus pneumoniae* are major causes of bacterial meningitis in children under five years of age. All these bacteria are protected from phagocytosis by a polysaccharidic capsule. Antibodies induced against the capsular polysaccharide (CPs) of the organism are protective in most cases. Effective Hib conjugate vaccines in which Hib CPs, PRP, is linked to different carrier proteins, such as diphtheria toxoid (PRP-D), tetanus toxoid (PRP-T), CRM 197 (HbOC) and the outer membrane proteins of *N. meningitidis* (PRP-OMP), have been developed. Four Hib conjugate vaccines are now commercially available. New glycoconjugate vaccines against *N. meningitidis* and *S. pneumoniae* are highly recommended by the American College of Physicians.

The development of multivalent pneumococcal vaccines for the prevention of both systemic and noninvasive pneumococcal diseases in infants, the elderly and immune-compromised individuals has gained increasing importance over the last decade. For more detailed reviews of pneumococcal disease, epidemiology, or the polysaccharide vaccine, numerous review articles are available (ref. 1, various references are referred to in parenthesis to more fully describe the state of the art to which this invention pertains. Full bibliographic information for each citation is found at the end of the specification, immediately preceding the claims. The disclosure of these references are hereby incorporated by reference into the present disclosure). *Streptococcus pneumoniae* is a capsulated, gram-positive bacterium that is present as normal flora in the human upper respiratory tract. It is a frequent and major cause of pneumonia, meningitis, bacteremia and noninvasive bacterial otitis media. Disease incidence is highest in infants and the elderly. In the United States alone, the overall incidence of systemic pneumococcal infections is estimated to be 50/100,000 in the geriatric population and 160/100,000 in children less than 2 years old (refs. 2, 3). Case fatalities can be as high as 40,000/year, especially in the geriatric population. Many serotypes of *S. pneumoniae* are developing resistance to conventional antibiotic treatments. The incidence of otitis media in children approaches 90% by the age of 5 and the peak incidence occurs at 6 to 15 months of age. It was estimated that over 1.2 million cases of otitis media occur annually. Recent studies on the epidemiology of pneumococcal disease (ref. 4) have shown that five serotypes (6B, 14, 19F, 23F and 18C) of the 85 known serotypes account for 70 to 80% of pneumococcal disease in infants and that in the United States, types 9V and 4 are ranked sixth and seventh. In Europe and developing countries, types 1 and 5 are more prevalent than types 4 and 9V. Thus, a pneumococcal conjugate vaccine for the United States should contain at least seven serotypes (4, 6B, 9V, 14, 18C, 19F, and 23F) to achieve a 75 to 85% coverage. Conjugate vaccine formulations for Europe and elsewhere should include serotypes 1, 5, 6B, 14, 18C, 19F and 23F. A broad-spectrum multivalent pneumococcal conjugate vaccine should then contain CPs from nine serotypes 1, 4, 5, 6B, 9V, 14, 18C, 19F, and 23F.

*N. meningitidis* is a gram-negative bacterium that has been serologically classified into groups A, B, C, 29e, W135, X, Y and Z. Additional groups (H, I, and K) were isolated in China and group L was isolated in Canada. The grouping system is based on the capsular polysaccharides of the organism. In contrast to the pneumococcal vaccine, the composition of the meningococcal polysaccharide vaccine has been greatly simplified by the fact that fewer polysaccharides are required. In fact groups A, B, and C are responsible for approximately 90% of cases of meningococcal meningitis. Prevention of group A and C meningococcal meningitis can be achieved by vaccination with a bivalent polysaccharide vaccine. This commercial vaccine has been used successfully in adults during the last decade to prevent major meningitis epidemics in many parts of the world. However, there is a need to improve this vaccine because a significant proportion of cases of meningococcal meningitis are due to serotypes other than A and C. Group B *N. meningitidis* is of particular epidemiologic importance, but groups Y and W135 are also significant. Although a tetravalent vaccine comprising groups A, C, W135, and Y polysaccharides is the current meningococcal meningitis vaccine, it is not very effective in young infants, since maturation of the immune response to most capsular polysaccharides in infants occurs around the age of 2 years.

The Group B meningococcal polysaccharide is poorly immunogenic in man. Two major reasons have been proposed to account for this phenomenon. One is that the α-(2→8)-linked sialic acid homopolymer is rapidly depolymerized in human tissue by neuraminidase. The other one is that Group B capsular polysaccharide is a polymer of N-acetylneuraminic acid (α 2->8 NeuNAc), and that the α 2->8 NeuNAc moiety is found as a monomer and dimer on several glycoproteins and gangliosides in adults and as a polymer of at least eight repeating units in rat fetal and newborn tissues. Thus, this structure is recognized as a "self" antigen by the human immune system. As a result, the production of antibody is suppressed or because of this molecular mimicry, a vaccine based on native Group B CPs might induce auto-antibodies directed against the α 2-8 NeuNAc moiety, and thus cause autoimmune diseases.

Since the Group B meningococcal CPs is not immunogenic in humans, approaches have been pursued to increase its immunogenicity. One approach uses non covalent complexes of Group B CPs and outer membrane protein (OMPs). Such complexes are formed by hydrophobic interaction between the hydrophobic regions of the OMPs and the diacyl glycerol group at the reducing end of the CPs. Human volunteers were given two doses of the complex at 0 and 5 weeks. Most individuals responded with an increase in antibodies to group B CPs. However, the second dose resulted in little or no increase in antibody titres which subsequently declined over a period of 14 weeks. The antibodies with group B polysaccharide specificity were limited to the IgM class and directed against determinants present only on high molecular weight polysaccharides.

To improve the immunogenicity of Group B CPs, Jennings (ref. 5) prepared a Group B meningococcal-tetanus toxoid conjugate (GBMP-TT) by covalently linking the CPs to tetanus toxoid (TT) through its terminal non-reducing sialic acid using periodate oxidized CPs. This procedure, however, did not result in any significant enhancement in CPs immunogenicity. The antibody response elicited in animals was found to be primarily directed against the linkage point between the CPs and the protein (GBMP-TT). Further improvement of the immunogenicity of group B CPs involved its chemical modification. Jennings (Ref. 6) reported that the N-acetyl groups of group B CPs could be selectively removed by the action of a strong base at elevated temperature. The acetyl groups were then replaced with N-propionyl groups by propionic anhydride treatment to produce N-propionylneuraminic acid ($\alpha$ (2->8) NeuPro) polymers. The N-propionylated CPs was first periodate oxidized with sodium periodate, and then coupled to TT in the presence of sodium cyanoborohydride to yield the chemically modified GBMP-TT conjugate. Mice immunized with this conjugate formulated in Freund's complete adjuvant (FCA), generated high levels of cross-reactive IgG antibody against native group B CPs. Murine anti-sera were found to be bactericidal for all group B strains. However, further studies revealed the existence of two populations of antibodies with different specificity. One population reacted with purified group B CPs whereas the other one did not. Antibodies that did not react with native group B CPs appeared to be responsible for bactericidal activity. These antibodies may recognize an epitope expressed by cell-associated CPs that is not present on purified CP. Alternative conjugates comprising the capsular polysaccharide of *N. meningitidis* group B CPs conjugated to a carrier protein as immunogenic compositions, including vaccines, and their use as and for the generation of diagnostic reagents, had been described by Kandil et al. (U.S. patent application Ser. No. 08/474,392 filed Jun. 7, 1995, assigned to the Assignee hereof and the disclosure of which is incorporated herein by reference, EP 0747063). In particular, the capsular polysaccharides of *N. meningitidis* contain multiple sialic derivatives that can be modified and used to attach carrier molecules.

The dramatic reduction in *Haemophilus influenzae* type b disease observed in countries that have licensed and used Hib CPs-protein conjugate vaccines, has demonstrated that CPs-protein conjugates can prevent systemic bacterial diseases. It is reasonable to expect that meningococcal and pneumococcal CPs-protein conjugates will also be efficacious. The possibility of preventing noninvasive diseases, such as otitis media, by systemic immunization with conjugate vaccines needs to be explored. Whether high titers of serotype-specific antibodies are sufficient to prevent either nasopharyngeal colonization and/or otitis media remains an open question. The development of an otitis media vaccine requires a multiple pneumococcal CPs-protein conjugates to elicit high anti-CPs antibody titers early in life.

The development of both multivalent pneumococcal and meningococcal CPs-protein conjugate vaccines to prevent systemic and noninvasive diseases presents many challenges to carbohydrate chemists, immunologists, clinicians and vaccine manufacturers. The amount of carbohydrate, the choice of carrier, the method of vaccine delivery, and the use of immuno stimulants or adjuvants are known to influence on the host immune responses. Immunogenic glycoconjugates can be formed between multifunctionalized CPs and proteins if the conditions are controlled very carefully. Most of the conjugates are today synthesized by coupling either CPs or oligosaccharides activated through the reducing end to a protein or peptide with or without a linker group.

A general glycoconjugation method involves random activation of the capsular polysaccharide or fragments of the polysaccharide by periodate treatment. The reaction leads to a random oxidative cleavage of vicinal hydroxyl groups of the carbohydrates with the formation of reactive aldehyde groups. Coupling to a protein carrier is by direct amination to the lysyl groups. A spacer group such as aminocaproic acid, can be reacted with the aldehydes by reductive amination and then coupled to the protein lysyl groups by water soluble carbodiimide condensation (ref. 7). The oligosaccharide-peptide conjugate reported by Paradiso (ref. 8) was prepared similarly except that a peptide presenting a T-cell epitope of $CRM_{197}$ was used instead of the native protein. Other conjugation approaches that have been disclosed by Gordon in U.S. Pat. No. 4,496,538 and by Schneerson et al. (ref. 9), involve directly derivatizing the CPs with adipic acid dihydrazide (ADH) following CNBr activation, and then conjugating the derivatized CPs directly to a carrier protein (D or T) by carbodiimide condensation. Marburg and Tolman (EP#534764A1) demonstrated that protein-dimeric CPs conjugate immunogens could be produced by coupling the first CPs to a protein carrier and then linking the second CPs to the first CPs via a bifunctional cross-linker.

Methods for inducing immunity against disease are constantly improving. Research has focused on the structure-function relationship of carbohydrate protein conjugates with the hope of discovering the mechanisms of B- and T-cell interactions with conjugates that could lead to vaccines with improved immunogenicity and to the development of adjuvants and delivery systems. Chong et al. (U.S. Pat. No. 5,679,352 assigned to the assignee hereof and the disclosure of which is incorporated herein by reference) showed that several factors affect the immunogenicity of carbohydrates. The minimum requirements for the synthesis of an immunogenic glycoprotein conjugate are that the B-cell epitope(s) of the CPs and the T-cell epitope(s) of the carrier should be functional after covalent linkage. The magnitude of the anti-CPs antibody response markedly depends on the spatial orientation of CPs relative to the T-cell epitopes. Anti-CPs antibody responses are enhanced when multiple antigenic peptides (MAPs) are used as carriers.

A single-dose polyvalent vaccine is listed as the first priority in the WHO vaccine development programme. A single-dose polyvalent CPs-protein conjugate vaccine (15 different CPs-protein conjugates: 1 Hib conjugate, five *N. meningitidis* conjugates and nine *S. pneumoniae* conjugates) against bacterial meningitis, presents a potential risk of hyperimmunization against classical carrier proteins, such as diptheria and tetanus toxoids. It is documented that non-epitope-specific suppression of the antibody response to Hib conjugate vaccines by pre-immunization with carrier proteins (ref. 11). Thus, appropriate approaches are required to solve this vaccine formulation problem. Some of the problems can be circumvented by incorporating conserved, cross-protective, non-capsular antigens from Hib, *N. meningitides* and *S. pneumoniae*. Although several outer membrane proteins have been proposed as vaccine candidates, none of them has been tested in clinical trials. A multiple CPs-carrier conjugate delivery system thus represents a novel generic approach and will be important in glycoconjugate vaccine development. Therefore, the present invention is directed towards novel glyconjugation technologies which can be used to prepare vaccines containing multiple oligosaccharides from different bacteria covalently linked to the same carrier protein or polypeptides.

SUMMARY OF THE INVENTION

In accordance with one aspect of the present invention, there is provided a multivalent immunogenic molecule, comprising a carrier molecule containing at least one functional T-cell epitope, and multiple different carbohydrate fragments each linked to the carrier molecule and each containing at least one functional B-cell epitope, wherein said carrier molecule imparts enhanced immunogenicity to said multiple carbohydrate fragments.

In one embodiment of the invention, the carbohydrate fragments are bacterial capsular oligosaccharide fragments. Such capsular polysaccharide fragments may be oligosaccharide fragments of *Streptococcus pneumoniae*, including fragments derived from at least two capsular polysaccharide of *S. pneumoniae* serotypes 1, 4, 5, 6B, 9V, 14, 18C, 19F and 23F. The carrier molecule may be a T-cell epitope-containing protein or protein fragment of *S. pneumoniae*.

The capsular polysaccharide fragments may be oligosaccharide fragment of *Neisseria meningitidis*, including fragments derived from at least two capsular polysaccharides of *N. meningitidis* Group A, B, C, W-135 and Y. The carrier molecule may be a T-cell epitope-containing protein or protein fragment of *N. meningitidis*.

The capsular polysaccharide employed in this aspect of the invention may be employed as oligosaccharide fragments sized from about 1 to about 5 kDa. Such fragments may be provided by acid hydrolysis of the capsular polysaccharide. The oligosaccharide fragments may be chemically modified for coupling to the carrier molecule.

The carrier molecule may be an oligopeptide containing at least one functional T-cell epitope or a carrier protein, such as tetanus toxoid.

In another embodiment of the invention, the carbohydrate fragments are fragments of carbohydrate-based tumor antigens. Such carbohydrate-based tumor antigen may be Globo H, $Le^Y$ or STn.

In accordance with another aspect of the invention, there is provided a method of forming a multivalent immunogenic molecule, comprising treating at least two different carbohydrate molecules to obtain carbohydrate fragments thereof, and conjugating each of the carbohydrate fragments to a carrier molecule.

In one embodiment, the carbohydrate molecule is a capsular polysaccharide of a bacteria and oligosaccharide fragments of the capsular polysaccharide are selected sized from 2 to 5 kDa. Such oligosaccharide fragments generally are derived from at least two different serotypes of the same bacteria, including *S. pneumoniae* and *N. meningitidis*.

In this embodiment of the present invention, such multivalent immunogenic molecules may be provided by glycoconjugation wherein three or more chemically-activated capsular polysaccharides or their derivatives simultaneously to a single carrier molecule, providing a random conjugation. This procedure is illustrated in FIG. 1.

In this embodiment of the invention, rational design of lysine-branched peptide systems may be employed for site-directed glycoconjugation. Using different side-chain protecting groups for lysine and cysteine residues during peptide synthesis, activated oligosaccharides may be selectively and sequentially linked to the same carrier through such residues. This procedure is illustrated in FIGS. 2A and 2B.

The method of site-directed conjugation may comprise first forming a multiple antigen peptide as the carrier molecule and anchored to a polymeric anchor wherein at least two carrier peptide segments have different terminal protecting groups. One of the protecting groups then is selectively removed and a first one of the oligosaccharide fragments is coupled to the unprotected carrier peptide segment. Another of the protecting groups is selectively removed and a second one of the oligosaccharide fragments to the unprotected carrier peptide segment. This procedure may be repeated for as many carrier peptides as is provided. The resulting molecule is severed from the polymeric anchor.

In accordance with a further aspect of the invention, there is provided an immunogenic composition for meningitis, comprising (1) a multiple pneumococcal glycoconjugate wherein the capsular oligosaccharide fragments are capsular oligosaccharide fragments of *Strepococcus pneumoniae*, (2) a multiple meningococcal glycoconjugate wherein the polysaccharide fragments are capsular oligosaccharide fragments of *Neisseria meningitidis*, and (3) an immunogenic synthetic PRP-peptide conjugate.

The multiple pneumococcal glycoconjugate may be derived from at least two capsular polysaccharides of *S. pneumoniae* serotypes 1, 4, 5, 6B, 9V, 14, 18C, 19F and 23F. The multiple meningococcal glycoconjugate may be derived from at least two capsular polysaccharides of *N. Meningitidis* Groups a, B, C, W-135 and Y.

Such universal meningitis immunogenic composition may be combined with other antigens, such as DTP-polio, to provide a polyvalent vaccine.

The present invention further includes a method of generating an immune response in a host by administering to the host an immunoeffective amount of an immunogenic composition of the present invention.

The present invention further includes diagnostic procedures and kits using the multivalent immunogenic molecule herein. Accordingly, in an additional aspect of the invention, there is provided a method of determining the presence of antibodies specifically reactive with a multivalent immunogenic molecule as provided herein:
  (a) contacting the sample with said multivalent immunogenic molecule to produce complexes comprising the molecule and any said antibodies present in the sample specifically reactive therewith; and
  (b) determining production of the complexes.

In a further aspect of the invention, there is provided A diagnostic kit for determining the presence of a multivalent immunogenic molecule as provided herein, comprising:
  (a) the multivalent immunogenic molecule;
  (b) means for contacting the multivalent molecule with the sample to produce complexes comprising the multivalent molecule and any said antibodies present in the sample; and
  (c) means for determining production of the complexes.

The present invention, therefore, permits pneumococcal glycopeptide conjugates to be used in a diagnostic immunoassay procedure or kit to detect the presence of anti-pneumococcal protein and CPs antibodies, for example, anti-CPs 1, 4, 5, 6B, 9V, 14, 18C, 19F and 23F and anti-pneumococcal surface protein A antibodies, or anti-meningococcal protein and CPs antibodies, for example, anti-CPs A, B, C, Y and W-135 and anti-meningococcal OMP class 1 antibodies.

In an additional aspect of the invention, there is provided a method of determining the presence of multivalent immunogenic conjugate molecule in a sample, comprising the steps of:
  (a) immunizing a subject with the immunogenic conjugate molecule to produce antibodies specific for the carbohydrate fragments;
  (b) isolating the carbohydrate fragment specific antibodies;
  (c) contacting the sample with the isolated multivalent immunogenic molecule present in the sample and said isolated carbohydrate fragment specific antibodies; and (d) determining production of the complexes.

A further aspect of the invention provides a diagnostic kit for determining the presence of a multivalent immunogenic molecule in a sample, comprising:

(a) antibodies specific for carbohydrate fragments of the multivalent immunogenic molecule;

(b) means for contacting the antibodies with the sample to produce a complex comprising multivalent immunogenic molecule and the antibodies; and (c) means for determining the production of the complex.

The present invention also extends to the use of a mixture of anti-PRP, anti-pneumococcal CPs and anti-meningococcal CPs antibodies as a component in a diagnostic immunoassay kit to detect the presence of Hib, S. pneumoniae and N. meningitidis in biological specimens.

BRIEF DESCRIPTION OF THE FIGURES

The invention will be further understood from the following descriptions and specific Examples with reference to the Figures in which.

GENERAL DESCRIPTION OF INVENTION

As discussed above, the present invention is related to novel glycoconjugation technologies that can be used to covalently link either multiple oligosaccharides from bacteria such as H. influenzae, N. meningitidis, S. pneumoniae, E. coli, and Group B Streptococcus, or carbohydrate-based tumor antigens, to the same carrier protein or polypeptide(s) and to the multivalent molecules produced thereby.

The development of strong and long-lasting humoral immunity requires the recognition of foreign antigens by at least two separate subsets of lymphocytes. B-lymphocytes (B-cells, lymphocytes derived from bone marrows), are the precursors of antibody-forming cells, and T-lymphocytes (T-cells, lymphocytes derived from thymus) modulate the function of B-cells. Most CPs are T-cell independent antigens and are capable of directly stimulating B-cells to produce antibodies. In general, CPs induce B-cells to terminally differentiate into antibody-secreting cells (plasma cells), but antibody responses are short-lived and limited by the number of responsive B-cells. Proteins and peptides are T-cell dependent antigens, and contain epitope(s) that can form peptide:MHC class II complexes on a B-cell and trigger armed helper T-cells to synthesize both cell-bound and secreted cytokines (effector molecules) that synergize in B-cell activation and clonal expansion. CPs can be converted into T-dependent antigens by coupling to a carrier protein or T-cell epitope(s) (ref. 9; U.S. Pat. No. 4,496,538). By repeated immunization with CPs-protein conjugates, the B-cell population in the vaccinees enters not only antibody production, but also proliferation and maturation. As a results, there are more B-cell making anti-CPs antibodies and higher antibody titers as booster responses.

Rationale for Using Oligosaccharides as Antigens

Figure 1:
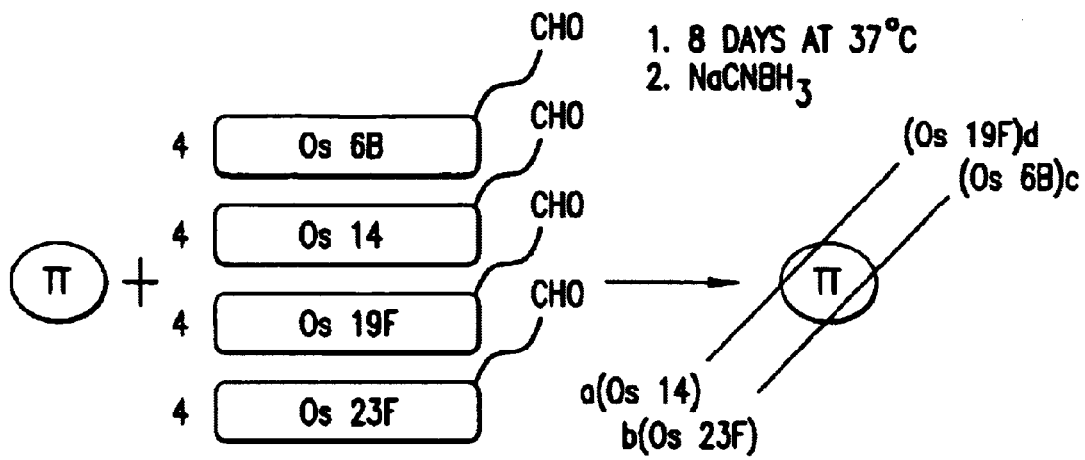
FIG. 1 shows a schematic diagram of several pneumococcal CPs randomly conjugated to a carrier protein, such as TT, and the procedure employed.
Figure 2A:
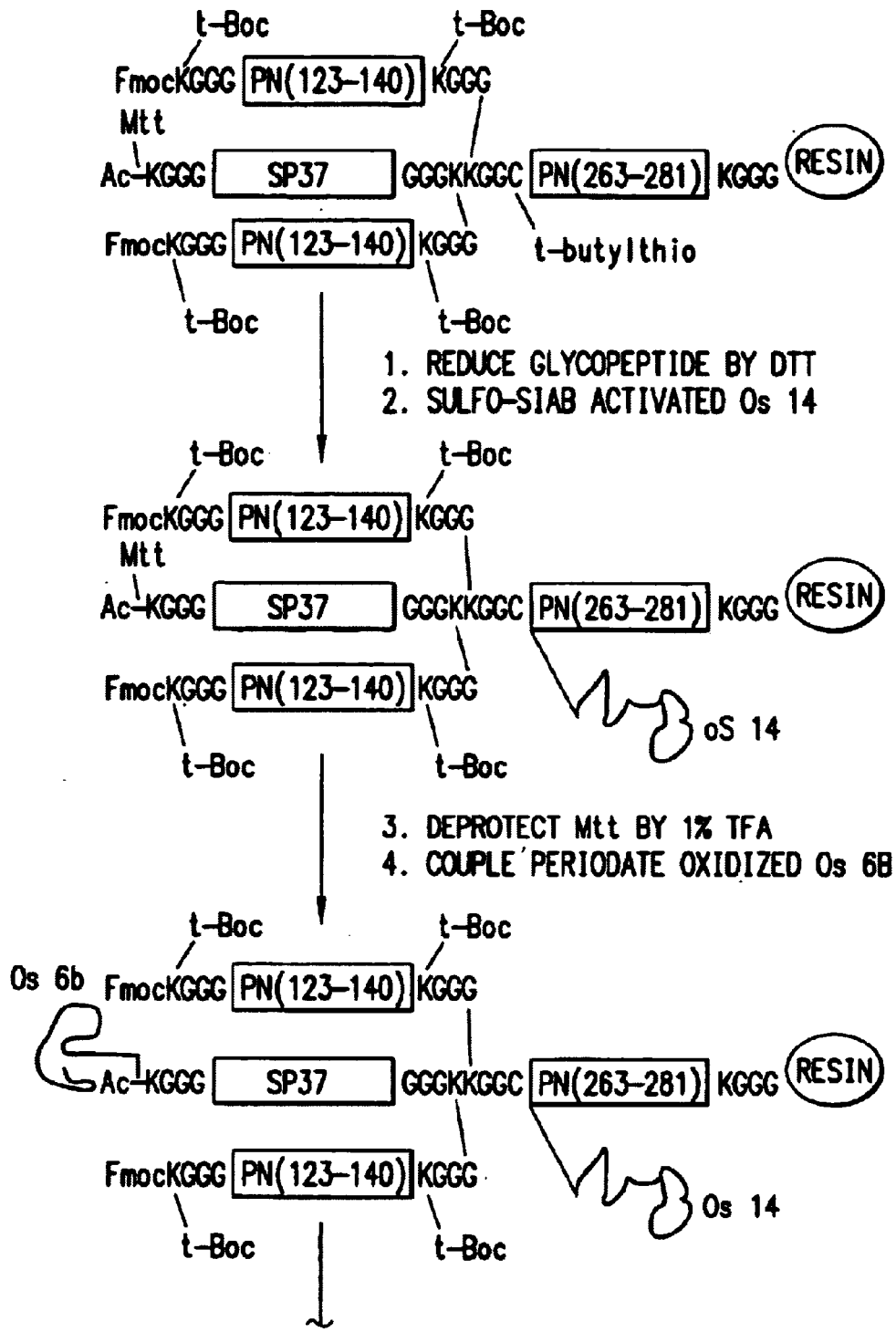
FIGS. 2A and 2B show a schematic diagram of the sequential cross-linking of chemically activated pneumococcal oligosaccharides to a lysine-branched peptide containing several functional T-cell epitopes from pneumococcal proteins.
Figure 2B:
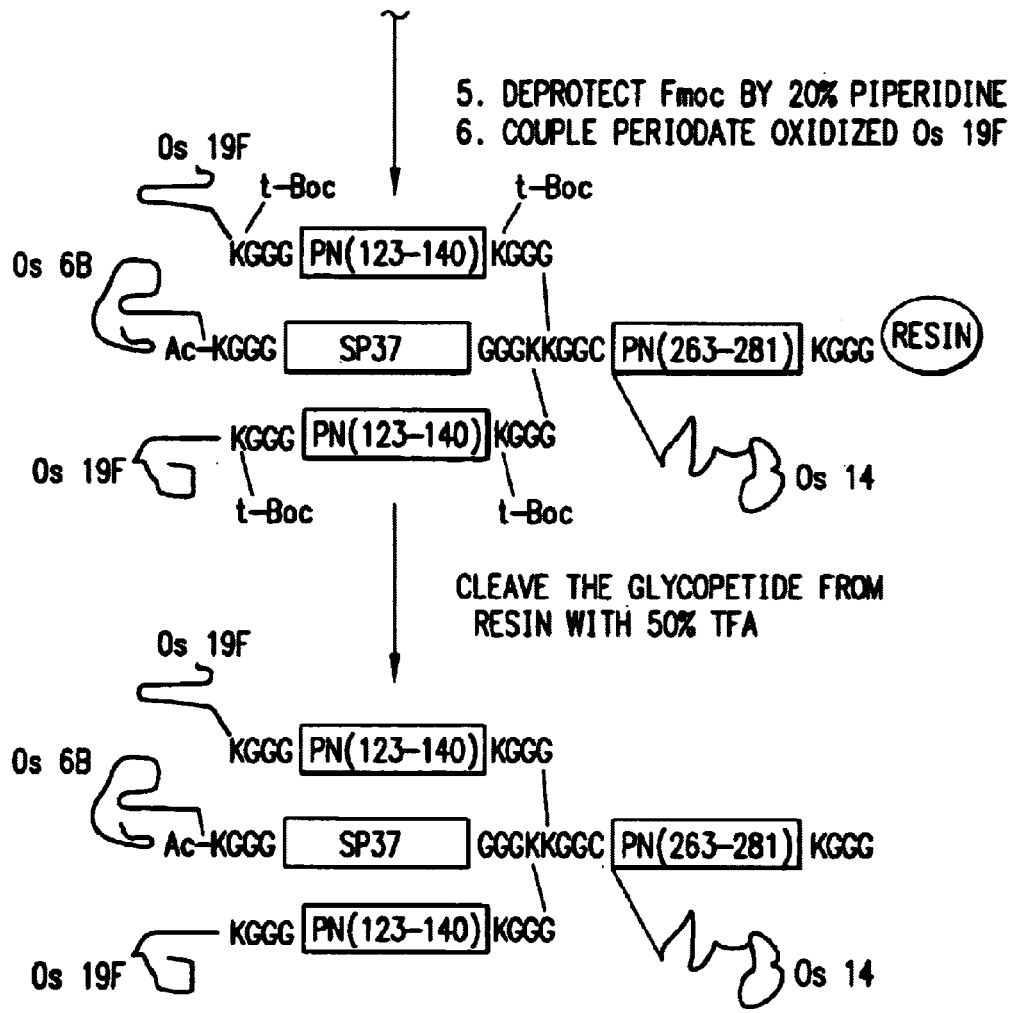

The minimum requirements for producing immunogenic glycoprotein conjugates are that the B-cell epitope(s) of the CPs and the T-cell epitope(s) of the carrier are functional after covalent attachment. To randomly conjugate two or more CPs to the same carrier protein or T-cell epitope(s), the size of the carbohydrate is reduced to about 2 kDa to about 5 kDa to prevent steric hindrance effects. At least two different approaches can used to covalently link multiple oligosaccharides to a carrier protein. The first approach is to activate or derivatize the oligosaccharides using the same chemistry, so that their conjugation to the carrier can be achieved simultaneously (FIG. 1). The second approach uses lysine-branched peptide systems for site-directed glycoconjugation. Using different side-chain protecting groups for lysine and cysteine residues during peptide synthesis, the activated oligosaccharides can be selectively and sequentially coupled to the same carrier protein via these residues (FIGS. 2A and 2B).

Preparation of Oligosaccharides

Figure 3:
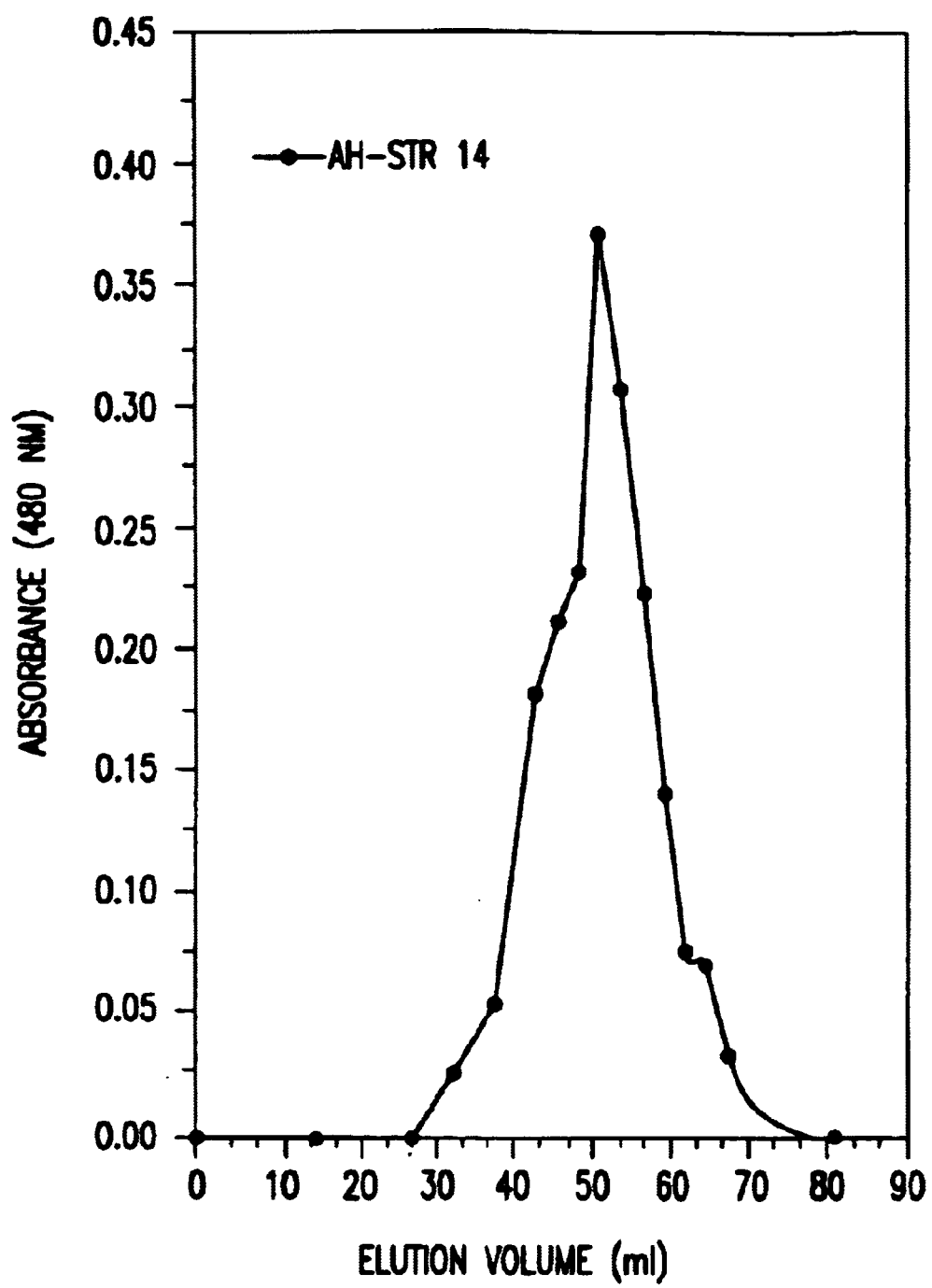
FIG. 3 shows the elution profile obtained during purification of acid-hydrolysed oligosaccharides of S. pneumonaie 14 using gel permeation chromatography on a Sephadex®-G100 column.

As described in detail in the Examples below, acid hydrolysis of various serotypes of Streptococcus pneumoniae capsular polysaccharides (>50 kDa) may be carried out to form oligosaccharides with a molecular weights ranging from about 2 to about 5 kDa. This process may comprise three steps: (1) acid hydrolysis of CPs in sealed vial under argon, (2) lyophilization and (3) purification of oligosaccharides by gel-filtration chromatography. The protocol for acid hydrolysis of CPs from S. pneumoniae serotypes 1, 4, 5, 9V and 14 has been optimized. Typically, CPs (2 mg/mL) are incubated in 0.5 M trifluoroacetic acid (TFA) at about 50° to about 90° C. for about 5 to about 10 hours. Since CPs from serotypes 6B and 19F contain labile phosphodiester bonds, their hydrolysis is performed under mild acid conditions (about 10 to about 50 mM acetic acid) at about 50° to about 100° C. for about 30 to about 48 hours. The CPs of serotype 23F can be partially hydrolyzed by either incubating in about 0.1 to about 0.5 M trifloroacetic acid (TFA) at about 70° C. for about 2 to about 4 hours or in about 1 to about 50 mM acetic acid at about 80° to about 110° C. for about 40 to about 60 hours. At the end of each hydrolysis, the reaction solutions are diluted 5-fold with water, then lyophilized. The purification of the crude oligosaccharides can be accomplished using Sephadex® G-100 gel filtration chromatography (about 2×about 210 cm column). Typical chromatographic results are illustrated in FIG. 3. The fractions are assayed for the presence of carbohydrate using the resorcinol/sulfuric acid assay (Ref. 1). The elution profile is plotted, and the chromatographically purified oligosaccharides with a mean mass of about 2 to about 5 kDa are pooled. Molecular weight markers used to calibrate the column are: dextran standards (39,100 and 8,800 Da), synthetic PRP hexamer (2,340 Da), sucrose (342 Da) and glucose (180 Da). Sized oligosaccharides of about 2 to about 5 kDa contain about 4 to about 8 repeating units in general and are expected to contain at least one B-cell epitope. The yields are about 70 to about 90%. These chromatographically purifed oligosaccharides are then used to prepare glycoconjugates comprised of multiple-oligosaccharides covalently linked to a carrier protein or a multiple antigen peptide system (MAP) containing T-cell epitopes from S. pneumococcal proteins.

Figure 4:
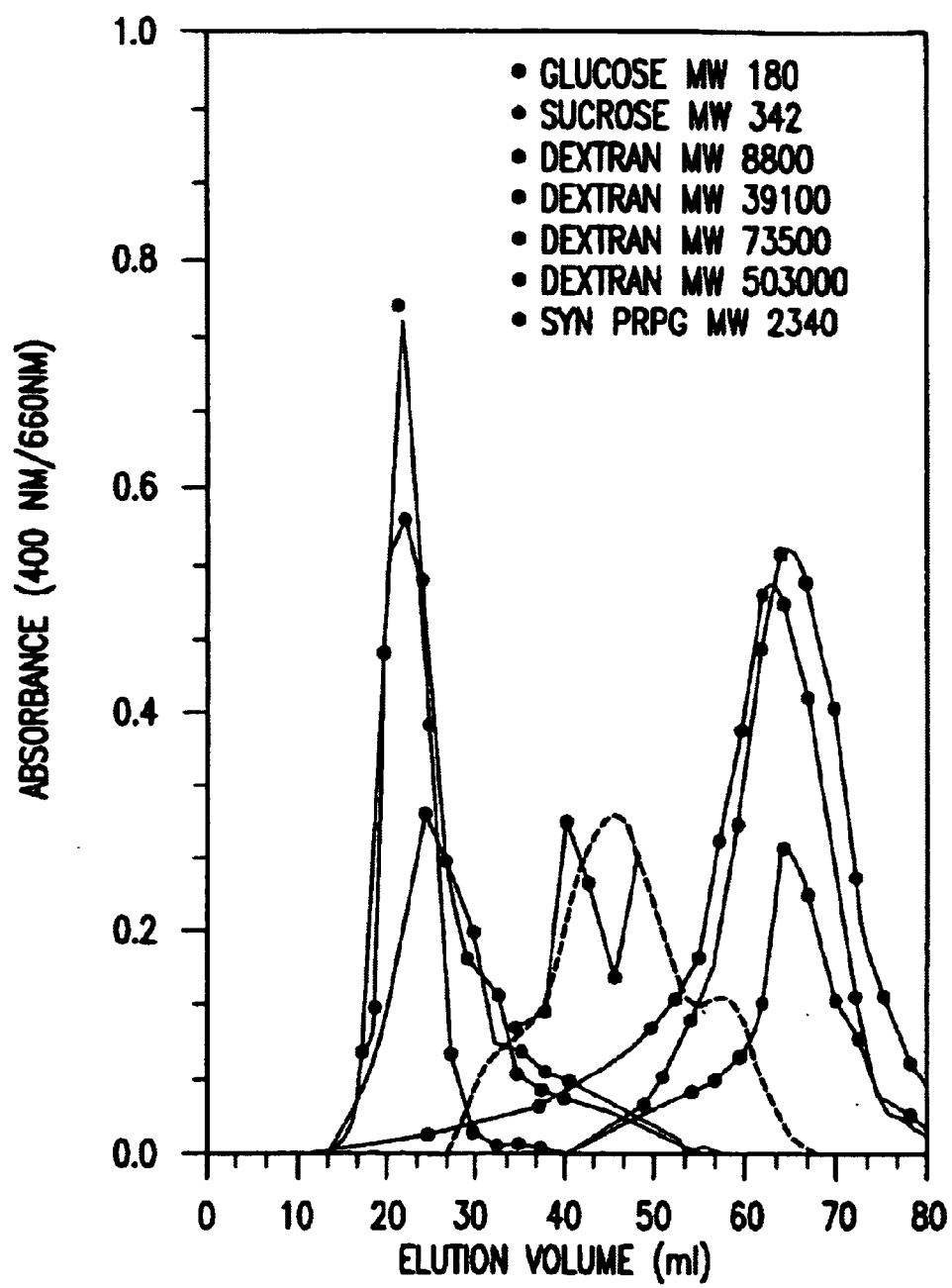
FIG. 4 shows the elution profile obtained during purification of the acid-hydrolysed oligosaccharides of N. meningitidis group B using a Sephadex®-G100 gel permeation chromatography.

As described in detail in the Examples below, acid hydrolysis of various serotypes of N. meningitidis capsular polysaccharides (>10 kDa) may be carried out to form oligosaccharides with a mean molecular weight of about 2 to about 5 kDa. In common with the acid hydrolysis of pneumococcal CPs, the process comprises acid hydrolysis, lyophilization and purification using gel-filtration chromatography. The conditions for acid hydrolysis of CPs from N. meningitidis groups C, W-135 and Y have been optimized. Typically, CPs (10 mg/mL) are mixed with about 20 to about 80 mM sodium acetate, pH about 4.5 to about 5.5, in sealed vials under argon at about 65° to about 100° C. for about 8 to about 12 hours. Since group B CPs can undergo intramolecular esterification under acidic conditions, The conditions used for CPs group C hydrolysis are employed, but the incubation time is limited to about 1 hr and the pH of the reaction is immediately adjusted to pH 7 with about 0.1 M NaOH to reverse the esterification process. Group A CPs contain labile phosphodiester bonds, thus they are hydrolyzed under mild acidic condition (such as about 10 to about 20 mM acetic acid) and incubated at about 50° to about 100° C. for about 30 to about 48 hours. At the end of each hydrolysis, the reaction solutions are diluted 5-fold with water and then lyophilized. The crude oligosaccharides are fractioned by Sephadex® G-100 gel filtration chromatography (about 2×about 210 cm column, see above). Typical chromatographic results are illustrated in FIG. 4. The fractions are assayed for the presence of sialic acid using the resorcinol/sulfuric acid assay (ref. 12). The elution profile is plotted, and chromatographically purified oligosaccharides of about 2 to about 5 kDa are pooled. Sized oligosaccharides typically contain about 6 to about 15 repeating units and are expected to contain at least one B-cell epitope. The yields are about 40 to about 80%. These chromatographically-purifed oligosaccharides are used to prepare glycoconjugates comprised of multiple-oligosaccharides covalently linked to a carrier protein or a multiple antigen peptide system (MAP) containing T-cell epitopes from meningococcal proteins.

Similar procedure may be used for capsular polysaccharides of other bacteria.

Carrier Selection.

Although several pneumococcal and meningococcal membrane proteins, such as pneumolysin (ref. 13), pneumococcal surface protein A (PspA) (ref. 14), S. pneumoniae 37 kDa protein (SP37) (ref. 15), meningococcal transferrin-binding protein 2 (Tbp2) (ref. 16), meningococcal pilin (ref. 17), and class 1 proteins (ref. 18), have been identified as potential protective antigens, none of them so far has been tested in clinical trials. These proteins contain potential T-cell epitopes which have been identified using conventional algorithms. Therefore, a panel of potential peptide carriers may be selected for conjugation with the meningococcal and pneumococcal oligosaccharides to form the multivalent immunogenic molecules herein.

In the present invention, peptides (Table I; SEQ ID NOS: 1 to 8) to be coupled to oligosaccharides were chosen on the basis of either their potential T-helper cell stimulatory properties or their potential protective ability or the conservation of sequences that would be important to recall T-cell memory. NMTBP2 (SEQ ID NO: 1) is a peptide fragment of N. meningitidis Tbp2 protein and had previously been identified to contain both functional T-cell epitope(s) and a strain-specific protective B-cell epitope recognized by a Tbp2-specific MAb (U.S. patent application Ser. No. 08/337,483, assigned to the assignee hereof and the disclosure of which is incorporated herein be reference; WO95/13370). Peptides NMC-1 and -2 (SEQ ID NOS: 2 and 3) were identified to contain the immunodominant human T-cell epitopes of N. meningitidis class 1 protein (ref. 19). NMPi-1 (SEQ ID NO: 4) was derived from N. meningitidis pilin protein and shown to contain sequences involved in adhesion (ref. 17). Peptides PN(123–140; SEQ ID NO: 5) and PN(263–281; SEQ ID NO: 6) derived from S. pneumoniae pneumolysin, both contain with funtional T-cell epitopes (ref. 20). SP37 (SEQ ID NO: 7) is the N-terminal fragment of from S. pneumoniae 37 kDa protein and shown to be highly immunogenic in rabbit immunogenicity studies. PSP-AA (SEQ ID NO: 8) is the N-terminal fragment of from S. pneumoniae PSPA protein and shown to be capable of eliciting protective immune responses in mice against live pneumococcal bacterial challenge (ref. 14).

Immunogenicity of Multi-oligosaccharide-carrier Conjugates in Animal Models.

A. Random conjugation approach (FIG. 1)

In the present invention, acids have been used to hydrolyze bacterial capsular polysaccharides to low-molecular-weight oligosaccharide fragments. The oligosaccharides can be purified and reacted with either ammonia or diaminoethane to generate a free terminal amino group at their reducing ends. The amino groups are reacted with an excess of the disuccinimidyl ester of adipic acid to introduce an active succinimidyl ester group. The activated oligosaccharides are then reacted with the free amino groups of carrier proteins or peptides to form covalent amide bonds. The glycoconjugates comprise at least two oligosaccharides coupled per protein/peptide molecule.

To avoid anti-linker antibody responses, oligosaccharides can be directly coupled to the carriers using the reductive amination procedure described by Jennings and Lugowsky (ref. 6). Advantages of this latter procedure are that linker molecules are unnecessary, thus eliminating the formation of potential neoantigen groups, and that a very stable secondary amine or in some cases a tertiary amine linkage, is formed between the saccharide and the protein. In addition, treatment of most meningococcal and pneumococcal capsular polysaccharides with periodate does not cause a reduction in molecular weight of the polysaccharide or fragment since oxidation takes place either on branch side chains or on cyclic sugar residues of the main chain. In either case, the main chain is not cleaved and the molecular size remains intact.

Figure 5:
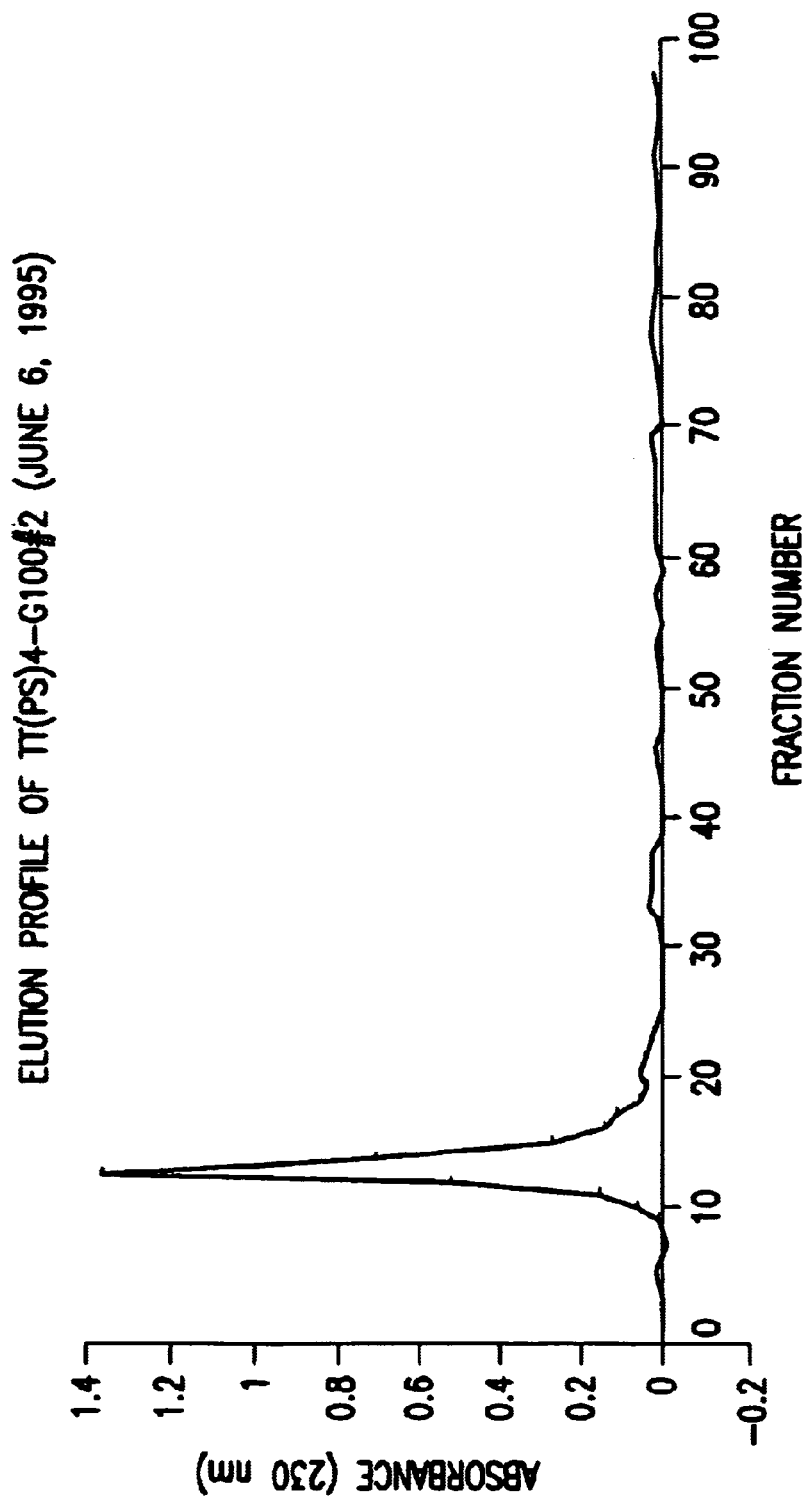
FIG. 5 shows an elution profile obtained during purification of multivalent S. pneumoniae oligosaccharides-TT conjugates.
Figure 6:
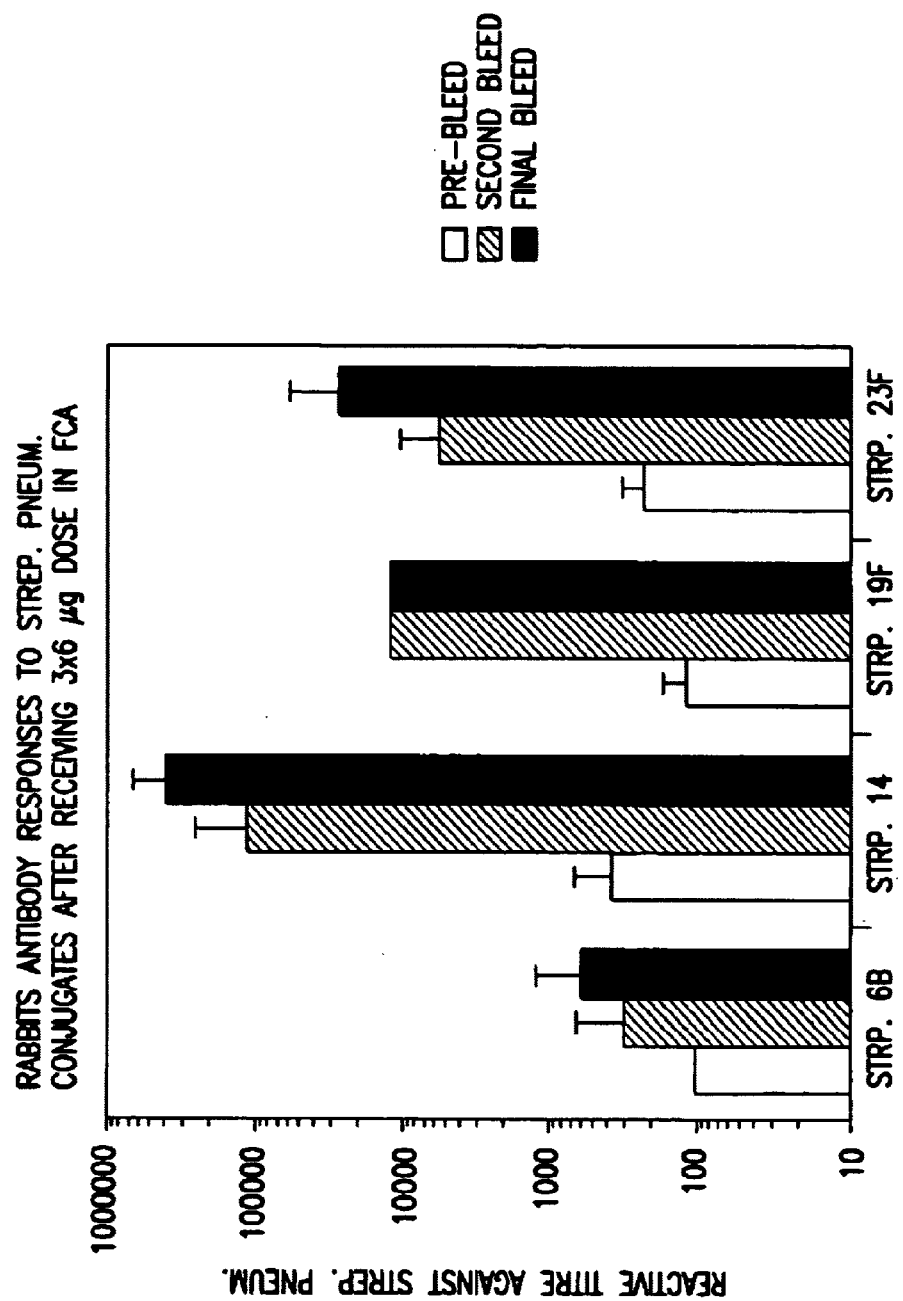
FIG. 6 shows rabbit antibody responses to multivalent S. pneumoniae oligosaccahrides-TT conjugates formulated in FCA.
Figure 7:
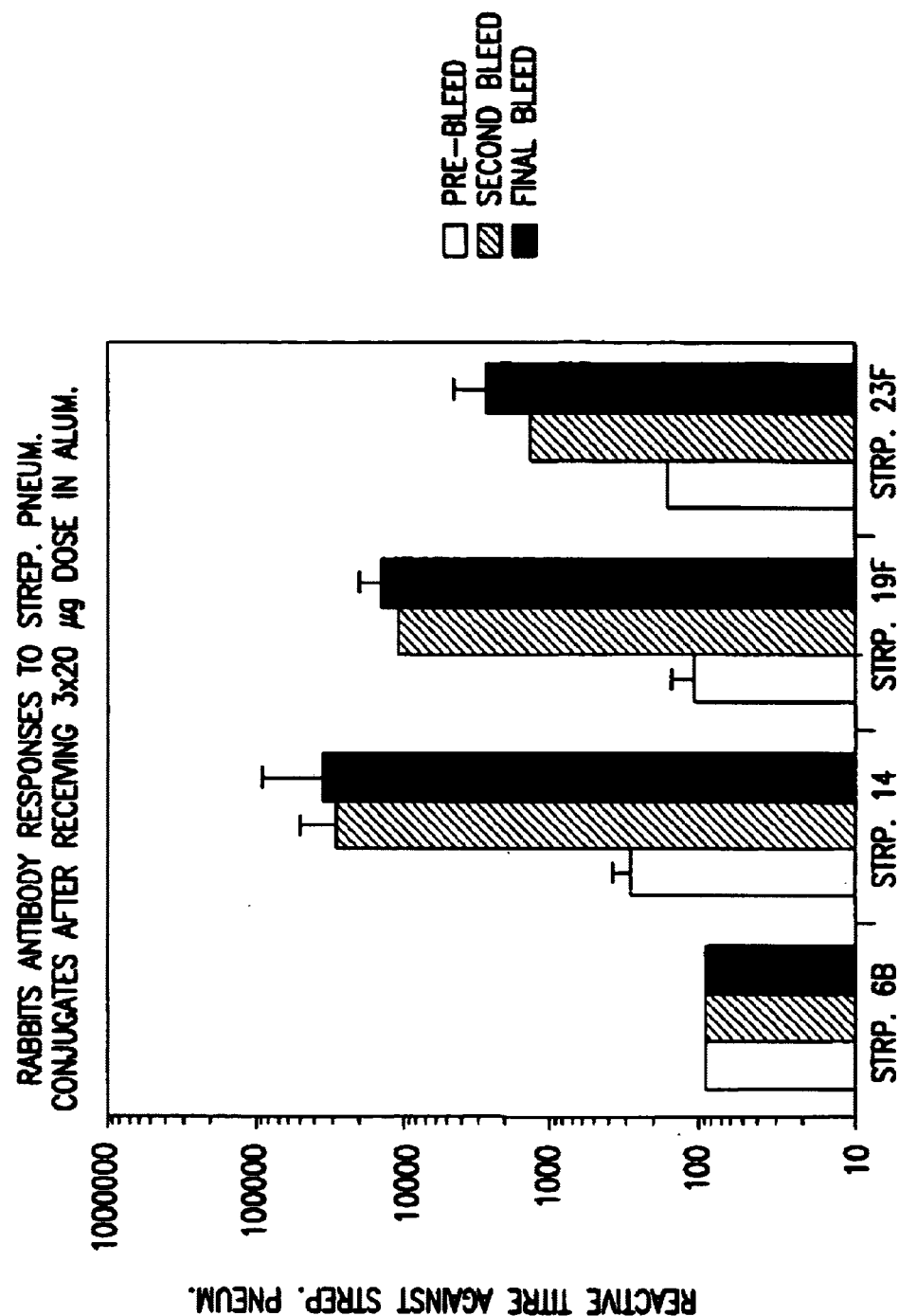
FIG. 7 shows rabbit antibody responses to multivalent S. pneumoniae oligosaccahrides-TT conjugates formulated in alum.
Figure 8:
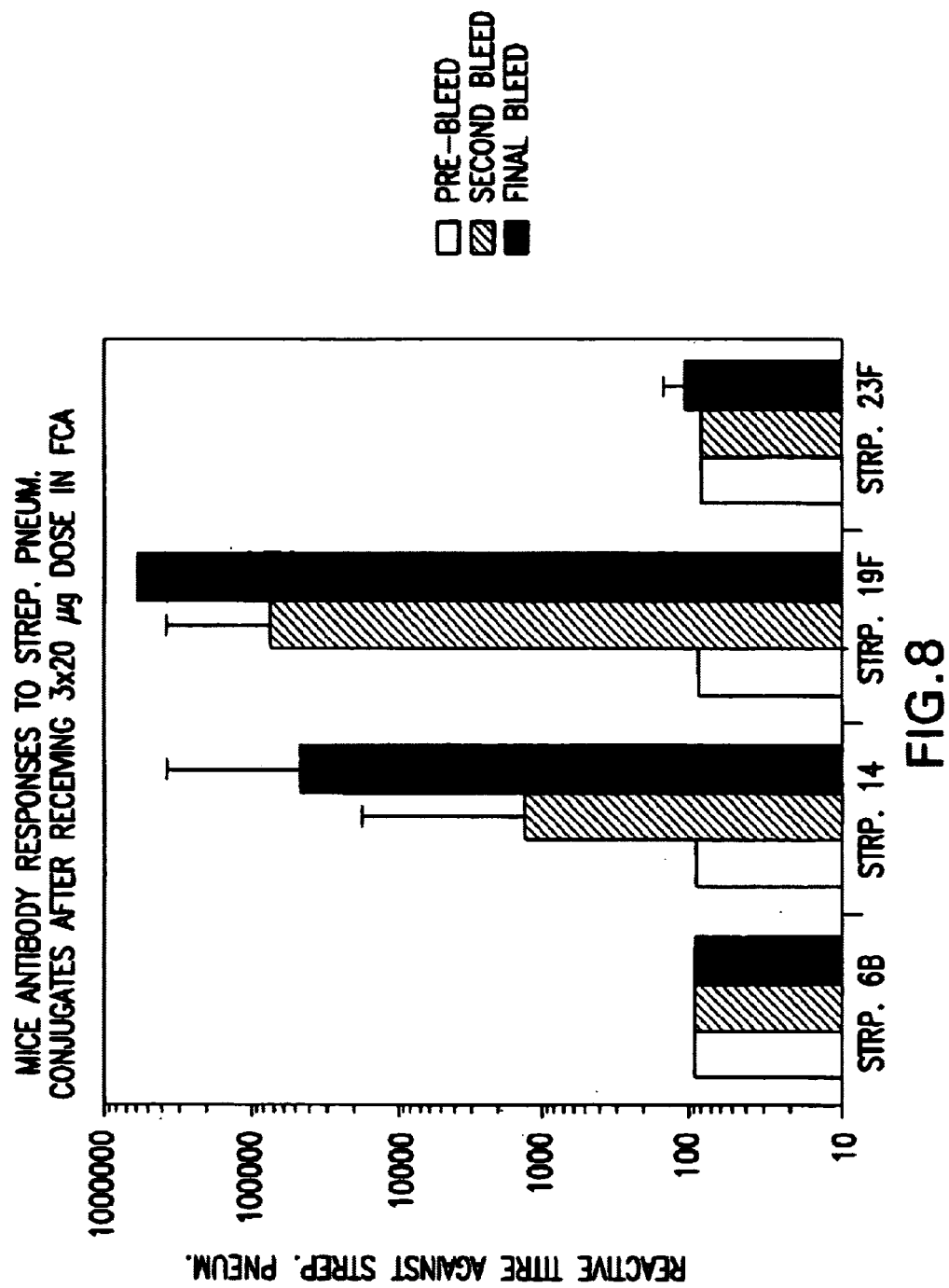
FIG. 8 shows mouse antibody responses to multivalent S. pneumoniae oligosaccahrides-TT conjugates formulated in FCA.

To evaluate the potential use of the multivalent molecules of the present invention, oligosaccharides from S. pneumoniae serotypes 6B, 14, 19F and 23F were randomly and covalently linked to TT, as shown in FIG. 1. The resulting multiantigenic glycoconjugate (MAG) was purified by the gel-filtration chromatography (FIG. 5). Protein and carbohydrate analyses revealed that the carbohydrate to protein molar ratio was 7.1:1. Four individual conjugates (6-TT, 14-TT, 19F-TT and 23F-TT) were prepared from fragments of the four respective serotypes with the same method for comparative studies. The multiple antigenic glycoconjugate (MAG) was formulated either with Freund's complete adjuvant (FCA) or alum. Results from rabbit and mouse (BALB/c) immunogenicity studies indicated that:

a. Strong antibody responses to all four serotype CPs were observed in rabbits when FCA was used as adjuvant (FIG. 6). Titers were comparable to those obtained with individual conjugates.
b. When alum was used as adjuvant in rabbits, only anti-14, -19F and -23F antibody responses were observed and no anti- 6B was found (FIG. 7).
c. Only anti-14 and 19F antibodies were elicited in BALB/c mice (FIG. 8).

The biological activity of anti-pneumococcal antibodies can be assayed by two different methods: in vitro opsonophagocytic assays and in vivo animal protection studies using either active or passive immunization. Previous studies (refs. 21 and 22) have shown that anti-*S. pneumococcal* CPs antibodies were biologically active and protective. There was a direct correlation between the total Ig antibody ELISA titers and opsonization titers. Therefore, the *pneumococcal* MAG candidate vaccine which can elicit anti-*S. pneumoniae* CPs antibody responses in animal models, will be useful for human immunization.

Figure 9:
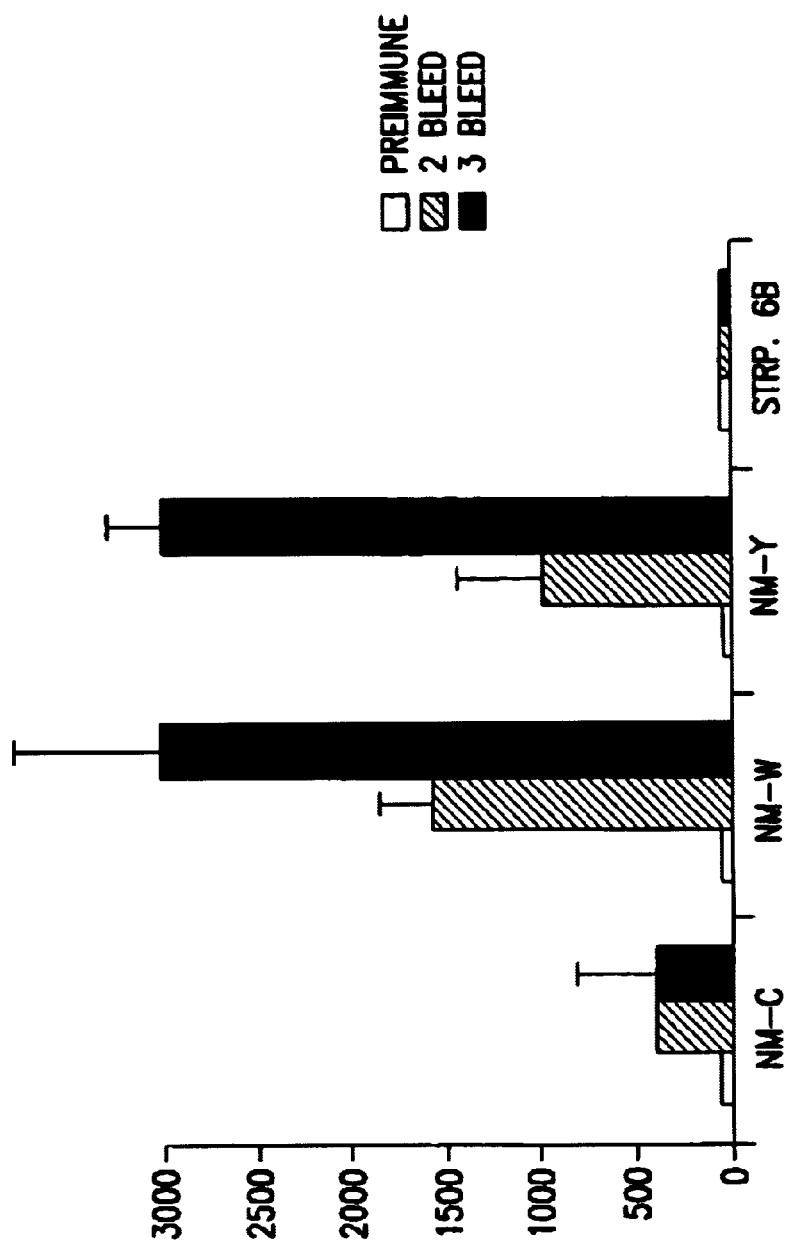
FIG. 9 shows rabbit antibody responses to multivalent N. meningitidis oligosaccahrides-TT conjugates formulated in FCA.

An *N. meningitidis* glycoconjugate containing group C, W and Y oligosaccharides was prepared as described above following the procedure shown schematically in FIG. 1. The multiple antigenic glycoconjugate was purified by gelfiltration chromatography. The molar ratio of carbohydrate to protein was found to be 6.6:1. Rabbit immunogenicity studies revealed that meningococcal MAG could elicit antibody responses against all three polysaccharides (groups C, W and Y) in carbohydrate-specific ELISAs (FIG. 9), and that the antisera had no reactivity against *S. pneumoniae* 6B PC used as negative control. The reactivities of antibodies against groups W and Y were very similar (geometric mean titer (GMT) about 3000). Group C was less immunogenic in this multivalent glycoconjugate, with a GMT about 500.

B. Multiple antigenic peptide (MAP) approach (FIG. 2A and 2B).

In this invention, we provide methods to design and synthesize novel lysine-branching peptides containing different T-helper cell epitopes (multiple antigenic peptide, MAP) to which several different oligosaccharides can be selectively and sequentially coupled. To test this concept, resin-bound MAP was synthesized and characterized as shown below.

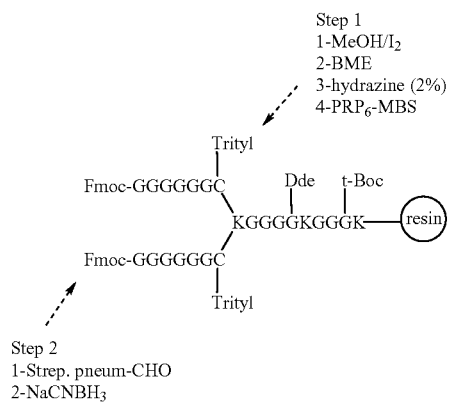

A Fmoc-Lys(t-Boc)-TGA resin (500 mg, purchased from BACHEM) with a substitution level of 180 µmol/g was used to prepare MAP. A standard Fmoc chemistry coupling protocol was used (4-fold excess of Fmoc-protected amino acids, O-benzotriazoyl-N,N,N',N'-tetramethyluronium hexafluorophosphate (HBTU) and N-hydroxybenzotriazole (HOBT)/diisopropylethylamine (DIEA) for 1 hr (Example 6)). In order to facilitate the conjugation of oligosaccharides, the substitution level of MAP was reduced to about 50 µmol/g when the first Fmoc-Gly residue was coupled. When the synthesis was completed, a small portion of MAP-resin was cleaved with 95% trifluroacetic acid (TFA) in the presence of ethane dithiol (EDT) and thioanisol. Amino acid analysis revealed that the cleaved MAP had the correct amino acid compositions.

MAP (150 mg) was treated with dithioanisol (DTT) in dimethyl formamide (DMF) to remove the trityl group from cysteine residues to conjugate oligosaccharides derivatized with SH-directed functional groups, such as m-maleimidobenzoyl-N-hydroxysuccinimide (MBS). After reduction, the resulting MAP resins were then assayed for amino groups and sulfydryl groups. From Ellam's assay the SH substitution level was found to be 64 µmol per g of MAP resin, and the degree of substitution of amino groups was found to be 71 µmol/g from the ninhydrin assay. These results indicated that trityl and Fmoc protecting groups could be quantitatively removed.

$(PRP)_6$-MBS which was prepared from a synthetic hexamer of 3-β-D-ribose-(1-1)-D-ribitol-5-phosphate derivatized with MBS (ref. 23), was dissolved in DMF/PBS solution and then coupled to the fully deprotected and reduced MAP under degassed conditions. After coupling, the MAP-$(PRP)_6$ was subjected to the Ellman's test for sulfhydryl group determination. The level of SH substitution was reduced to 6.85 µmol per g of resin. The coupling of PRP was independently confirmed by the ribose assay and was found to be 18 µg of $(PRP)_6$/mg resin.

The resulting MAP-$PRP_6$ was mixed with periodate oxidized *S. pneumoniae* serotype 19F (1 eq.) in methanol/phosphate buffer (pH 7.8) in the presence of $NaCNBH_3$ at 38° C. for 6 days. After conjugation, the amino group substitution determined by the ninhydrin assay was found to be 16 µmol per g of resin. Total sugar content was again found to be 16.1 mg/g resin. A small portion of 19F-$(PRP)_6$-MAP glycoconjugate-resin was cleaved with 95% TFA in the presence of ethane dithiol (EDT) and thioanisol. After the work-up, the MAP-glycoconjugate was found to have the correct amino acid composition and carbohydrate content. These results strongly suggest that different oligosaccharides can be selectively and sequentially conjugated to MAP resin.

Figure 10:
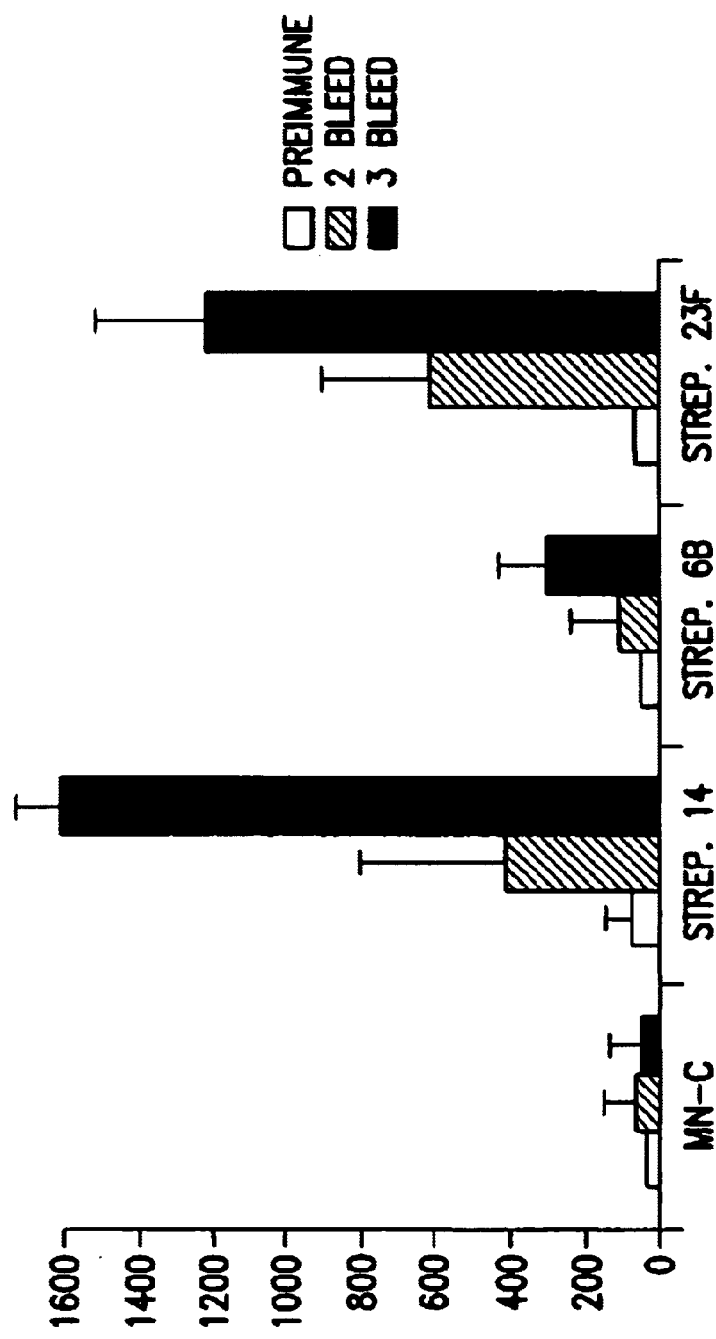
FIG. 10 shows rabbit antibody responses to multivalent S. pneumoniae glycopeptide conjugates formulated in FCA.

Before synthesizing a MAP resin containing different T-cell epitopes, periodate-oxidized pneumococcal oligosaccharides from serotypes 6B, 14 and 23F were tested for coupling efficiently to resin-bound linear peptides corresponding either to PN(123–140)(SEQ ID NO: 5) or PN(263–281) (SEQ ID NO: 6), which are T-cell epitopes derived from *S. pneumoniae* membrane protein pneumolysin. Linear glycopeptides 6B-PN(123–140), 14-PN(263–281) and 23F-PN(123–140) were prepared using reductive amination. The coupling efficiency of oligosaccharide to resin-bound peptide was found to be 10 to 30% as judged by the free amino group determination using the ninhydrin assay. The glycopeptides were cleaved from the resin using 95% TFA, then semi-purified by RP-HPLC. Rabbit immunogenicity studies were performed with an "equimolar" combination of these linear glycopeptides formulated in FCA/IFA. The results indicated that the glycopeptide conjugates were immunogenic and elicited anti-6B, anti-14 and anti-23F polysaccharide antibody responses (FIG. 10). In addition, rabbit antisera reacted with the peptides as judged by peptide-specific ELISAs (Table 2).

A MAP resin containing three T-cell epitopes derived from different *S. pneumococcal* membrane proteins was synthesized using a Fmoc-Gly-Lys-TGA resin with a substitution level of 50 μmol/g, as shown in the (FIGS. 2A and 2B). The whole synthesis was carried out manually using the optimized Fmoc chemistry coupling protocol described above. When the synthesis was completed, a small portion of MAP-resin was cleaved with 95% TFA in the presence of EDT and thioanisol, the cleaved MAP was found to have the correct amino acid compositions by amino acid analysis. The MAP resin was reduced by DTT to remove the t-butylthio protecting groups from the cysteine residues. After excess washing, the MAP resin was resuspended in a DMF/PBS solution, then mixed with a 4-fold excess of sulfosuccinimidyl (4-iodoacetyl amino benzoate (sulfo-SIAB) activated oligosaccharides from *S. pneumoniae* serotype 14 (Os14). After overnight mixing at room temperature, the MAP resin was collected by filtration and washed with PBS, DMF and then methanol. The MAP-Os14 resin was subjected to Ellman's test and sulfhydryl group determination. The level of SH substitution was found to be half of the starting value. Recoupling did not increase the amount of Os14 conjugated to the MAP resin. The presence of N-acetylgalactosamine (GlcNAc) in the glyco-MAP resin, a carbohydrate found in Os14, was independently confirmed by carbohydrate analysis. MAP-Os14 was first treated with 1% TFA to remove Mtt (a lysine-protecting group) from Mtt-lysine residues, then neutralized with a mild base, 1% diisopropylethylamine (DIEA)/DMF. The presence of free amino groups was assayed by the ninhydrine test which indicated that over 90% of Mtt groups had been removed. The MAP-Os14 resin was resuspended in PBS, and then mixed with four equivalents of periodate-oxidized *S. pneumoniae* serotype 6B oligosaccharides (Os6B) in DMF/phosphate buffer (pH 7.8) in the presence of NaCNBH$_3$ at 38° C. for 6 days. After conjugation, the substitution of amino groups was determined by the ninhydrin assay was found to be 80 to 90% of the original value. Again a double and triple coupling did not improve the conjugation of Os6B to the MAP-Os14 resin. Although the coupling efficiency was poor (about 15%), the presence of ribitol in the MAP conjugate, a carbohydrate found in Os6B, was confirmed by carbohydrate analysis.

Figure 11:
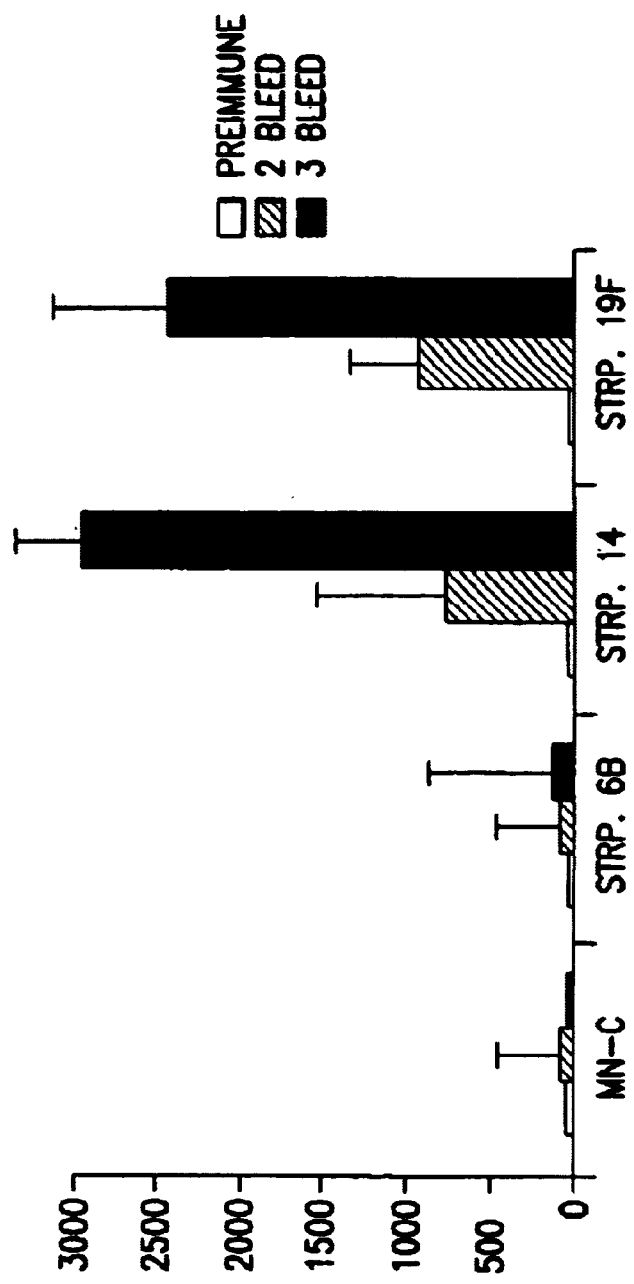
FIG. 11 shows rabbit antibody responses to multivalent S. pneumoniae oligosaccahrides-MAP conjugates formulated in FCA.

The MAP-Os14-Os6B conjugate was treated with 20% piperidine in DMF to remove the Fmoc protecting group from Fmoc-lysine residues. After washing, the MAP-Os14-Os6B resin were mixed with a 4-fold excess of periodate oxidized *S. pneumoniae* serotype 19F oligosaccharides (Os19F) in DMF/phosphate buffer (pH 7.8) in the presence of NaCNBH$_3$ at 38° C. for 6 days. After conjugation, the degree of amino group substitution measured by the ninhydrin assay was found to be about 90%. The coupling reaction was repeated and its efficiency was determined to be about 15%. However, the presence of N-acetylmannose (ManNAc), a sugar found in Os19F, was detected by carbohydrate analysis. A small portion of MAP glycoconjugate-resin was cleaved with 95% TFA in the presence of EDT and thioanisol. After the work-up, the MAP-glycoconjugate was assayed for amino acid composition and carbohydrate content, and found to have a correct amino acid composition and a correct carbohydrate content. Although the overall yield was very low (about 5%), these results nevertheless demonstrate that different oligosaccharides can be selectively and sequentially conjugated to a MAP resin. Furthermore, rabbit immunogenicity studies indicated that this MAP glycopeptide conjugate was immunogenic and elicited strong antibody responses against polysaccharides 19F and 14 (GMT about 3000), but very weak anti-6B IgG responses (FIG. 11). The antibody titers against 19F and 14 polysaccharides were significant lower than those obtained in rabbits immunized with multivalent oligosaccharides conjugated to TT (FIG. 7), but we still expect that the pneumococcal multivalent MAP conjugate candidate vaccine will be useful for human immunization. In addition, the rabbit antisera reacted strongly with the T-cell peptides in peptide-specific ELISAs (Table 3).

Utility of Synthetic Glycopeptide Conjugation Technology.

In preferred embodiments of the present invention, the glycoconjugate technology can be generally utilized to prepare conjugate vaccines against pathogenic encapsulated bacteria. Thus, the glycoconjugate technology of the present invention may be applied to vaccinations to confer protection against infection with any bacteria expressing potential protective polysaccharide antigens, including *Haemophilus influenzae, Streptococcus pneumoniae, Escherichia coli, Neisseria meningitidis, Salmonella typhi, Streptococcus mutans, Cryptococcus neoformans, Klebsiella, Staphylococcus aureus* and *Pseudomonas aerogenosa*.

In particular embodiments, the synthetic glycoconjugate technology can be applied to produce vaccines eliciting antibodies against proteins and oligosaccharides, such as Globo H, Le$^Y$ and STn. Such vaccines may be used, for example, to induce immunity against tumor cells, or to produce anti-tumor antibodies that can be conjugated to chemotherapeutic or bioactive agents.

It is also understood that within the scope of the invention are any variants or functionally equivalent variants of the above specific peptides. The terms "variant" or "functionally equivalent variant" as used above, mean that, if the peptide is modified by addition, deletion or derivatization of one or more of the amino acid residues, in any respect, and yet acts in a manner similar to the specific peptides described herein, then such modified peptide falls within the scope of the invention. Given the amino acid sequence of these peptides (Table 1) and any similar peptide, these are easily synthesized employing commercially available peptide synthesizers, such as the Applied Biosystems Model 430A, or may be produced by recombinant DNA technology.

It is clearly appears to one skilled in the art that the various embodiments of the present invention have many applications in the fields of vaccination, diagnosis and treatment of infection and the generation of immunological reagents. A further non-limiting discussion of such uses is further presented below.

Vaccine Preparation and Use

As indicated above, the present invention, in one embodiment, provides multivalent immunogenic conjugates useful for formulating immunogenic compositions, suitable to be used as, for example, vaccines. The immunogenic composition elicits an immune response by the host to which it is administered including the production of antibodies by the host.

The immunogenic compositions may be prepared as injectables, as liquid solutions or emulsions. The antigens and immunogenic compositions may be mixed with physiologically acceptable carriers which are compatible therewith. These may include water, saline, dextrose, glycerol, ethanol and combinations thereof. The vaccine may further contain auxiliary substances, such as wetting or emulsifying agents or pH buffering agents, to further enhance their effectiveness. Vaccines may be administered by injection subcutaneously or intramuscularly.

Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. Oral formulations may include normally employed incipients, such as pharmaceutical grades of saccharine, cellulose and magnesium carbonate.

These compositions may take the form of solutions, suspensions, tablets, pills, capsules, sustained release formulations or powders and contain 1 to 95% of the immunogenic compositions of the present invention.

The immunogenic compositions are administered in a manner compatible with the dosage formulation, and in such amount as to be therapeutically effective, protective and immunogenic. The quantity to be administered depends on the subject to the immunized, including, for example, the capacity of the subject's immune system to synthesize antibodies, and if needed, to produce a cell-mediated immune response. Precise amounts of antigen and immunogenic composition to be administered depend on the judgement of the practitioner. However, suitable dosage ranges are readily determinable by those skilled in the art and may be of the order of micrograms to milligrams. Suitable regimes for initial administration and booster doses are also variable, but may include an initial administration followed by subsequent administrations. The dosage of the vaccine may also depend on the route of administration and will vary according to the size of the host.

The concentration of antigen in an immunogenic composition according to the invention is in general 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.005 to 0.5 percent solution in phosphate buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune response.

Immunostimulatory agents or adjuvants have been used for many years to improve the host immune responses to, for example, vaccines. Intrinsic adjuvants, such as lipopolysaccharides, normally are the components be the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes;
(5) synergy with other adjuvants;
(6) capability of selectively interacting with populations of antigen presenting cells (APC);
(7) ability to specifically elicit appropriate T.1 or TH2 cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N glycosylcarbamates, each of which is substituted in the sugar residue by an amino acid, as immune-modulators or adjuvants. Thus, Lockhoff et al. (U.S. Pat. No. 4,855,283 and ref. 29) reported that N-glycolipid analogs displaying structural similarities to the naturally occurring glycolipids, such as glycosphingolipids and glycoglycerolipids, are capable of eliciting strong immune responses in both herpes simplex virus vaccine and pseudorabies virus vaccine. Some glycolipids have been synthesized from long chain alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. (ref. 30), reported that octodecyl esters of aromatic amino acids complexed with a recombinant hepatitis B surface antigen, enhanced the host immune responses against hepatitis B virus.

Immunoassays

In one embodiment, the conjugates of the present invention are useful for the production of immunogenic compositions that can be used to generate antigen-specific antibodies that are useful in the specific identification of that antigen in an immunoassay according to a diagnostic embodiment. Such immunoassays include enzyme-linked immunosorbent assays (ELISA), RIAs and other non-enzyme linked antibody binding assays or procedures known in the art. In ELISA assays, the antigen-specific antibodies are immobilized onto a selected surface; for example, the wells of a polystyrene microtiter plate. After washing to remove incompletely adsorbed antibodies, a nonspecific protein, such as a solution of bovine serum albumin (BSA) or casein, that is known to be antigenically neutral with regard to the test sample may be bound to the selected surface. This allows for blocking of nonspecific adsorption sites on the immobilizing surface and thus reduces the background caused by nonspecific bindings of antigens onto the surface. The immobilizing surface is then contacted with a sample, such as clinical or biological materials, to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove nonimmunocomplexed material. The washing procedure may include washing with a solution, such as PBS/Tween or a borate buffer.

Following formation of specific immunocomplexes between the antigen in the test sample and the bound antigen-specific antibodies, and subsequent washing, the occurrence, and even amount, of immunocomplex formation may be determined by subjecting the immunocomplex to a second antibody having specificity for the antigen. To provide detecting means, the second antibody may have an associated activity, such as an enzymatic activity, that will generate, for example, a colour development upon incubating with an appropriate chromogenic substrate. Quantification may then achieved by measuring the degree of colour generation using, for example, a visible spectra spectrophotometer. In an additional embodiment, the present invention includes a diagnostic kit comprising antigen-specific antibodies generated by immunization of a host with immunogenic compositions produced according to the present invention.

It is understood that the application of the methology of the present invention is within the capabilities of those having ordinary skills in the art. Examples of the products of the present invention and processes for their preparation and use appear in the following examples.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Immunological methods may not be explicitly described in this disclosure but are well within the scope of those skilled in the art.

Example 1

Preparation of Acid-hydrolyzed Group B Meningococcal (GBM) Oligosaccharides.

This Example describes a method for preparing GBM oligosccharides (M. wt. 3000 to 4500 Da) from the commercially available GBM polysaccharides (M. wt>10 KDa).

Reagents required:
1-GBM polysaccharides from Sigma cat # C-5762.
2-Sodium acetate (50 mM) buffer pH 5.00, prepared by mixing one volume of 0.5 M sodium acetate with one volume of 0.23M acetic acid.
3-Reaction vial and a magnetic stirring bar.
4-Sephadex G-25 gel column
5-Ammonium bicarbonate (20 mM)
Procedure:
The GBM polysaccharide (200 mg) was dissolved in 15 mL of degassed 50 mM sodium acetate buffer, pH 5.0 and the mixture was then stirred at 80° C. for 1 hr. The reaction mixture was then immediately cooled with ice and neutralized to pH 7.0 by dropwise addition of 0.1M NaOH. The total mixture was then lyophilized to yield a crude product (460 mg, containing sodium acetate) About 100 mg acid treated GBM were first dissolved in 3 mL of 20 mM ammonium bicarbonate and then loaded into a Sephadex G-25 gel column equilibrated with 20 mM ammonium bicarbonate solution using the following conditions:
Column: (10×1000 mm), calibrated with dextran 8800, β-cyclodextran and sucrose standards.
Flow rate: 0.6 mL/min.
Buffer: 20 mM ammonium bicarbonate.
Fraction collected at 4.5 min/tube.
The fractions were assayed for the presence of sialic acid using the resorcinol/sulfuric acid assay (ref. 12). The elution profile was then plotted and sialic acid-containing fractions with an average molecular weight of 4 kDa were pooled and lyophilized. The final yield of the acid hydrolyzed GBM was obtained.

Example 2

This Example Shows Chemical Modification of Acid-hydrolyzed GBM Oligosaccharides.

N-propionylated, acid-hydrolyzed GBM oligosaccharides were prepared according to the method previously described by H. Jennings et al. (ref. 6) with some modifications. The N-propionylated GBM oligosaccharides ultimately were coupled to a MAP backbone containing other oligosaccharide to produce multivalent multiple carbohydrate vaccines, as described below.
Reagents required:
1-Acid-hydrolyzed GBM oligosaccharides.
2-Sodium hydroxide (2 M solution).
3-Propionic anhydride (Aldrich).
4-Ammonium bicarbonate (10 mM)
5-Aqueous oxalic acid (50%)
6-Sodium borohydride (Sigma)
Procedure:
N-deacetylation of the acid-hydrolyzed GBM oligosaccharides:
N-deacetylated acid-hydrolyzed group B meningococcal polysaccharides was prepared according to the method described by Jenning et al., with three modifications;
1-The reaction was performed at ca 110° to 120° C.
2-The dialysis was performed using molecular porous membrane (1000 mol. wt. cut off).
3-The neutralization of sodium hydroxide was accomplished using 50% aqueous oxalic acid in the cold and last over 1 hr.
The polysaccharide (100 mg) was dissolved in 5 mL of degassed 2M sodium hydroxide containing sodium borohydride (10 mg). The resulting mixture was then heated for 6 to 8 hours at about 100° to 120° C. and the product was isolated by a combination of pH neutralization in an ice bath using oxalic acid 50%, followed by dialysis (four changes of 10 mM ammonium bicarbonate, 4° C.) and lyophilization to provide a product (65.2 mg). This de-acetylation resulted in 100% de-acetylation, as determined by complete disappearance of the acetyl signal in the $^1$H NMR spectrum.

Preparation of N-propionyl GBM Oligosaccharides

The N-deacetylated GBM oligosaccharide prepared from the previous step (55 mg) was dissolved in saturated sodium bicarbonate (12 mL) and three aliquots of propionic anhydride (0.250 mL) were added over 30 minutes period. The total mixture was then stirred overnight at room temperature. Ninhydrine test was performed and found to be negative indicating complete conversion of free amino groups to propionamido groups. The mixture was then dialyzed against distilled water (3×4 L) and lyophilized to afford the acid-hydrolyzed propionylated GBM oligosaccharide (43.2 mg).

Example 3

This Example Shows the Preparation of Oligosaccharides from *Streptococcus Pneumoniae*

This Example describes the general methods using acid hydrolysis of *Streptococcus pneumoniae* capsular polysaccharides (CP) (M. wt~50 kDa) to produce oligosaccharides with a molecular mass ranging from 2.5 to 5.0 kDa. The resulting oligosaccharides can be subjected to a novel glycoconjugation technology to prepare glycoconjugates containing multiple-oligosaccharides covalently linked to a carrier protein or a multiple antigen peptide system (MAP).

Reagents required:
1-CP serotypes 6B, 14, 19F and 23F (ATTC)
2-Acetic acid
3-Trifloroacetic acid
4-Gel chromatography column (Sephadex G-100, 10×1000 mm)
5-Round bottom flask (250 mL)
6-Magnetic stirring bar
7-Oil bath Procedure:
In a round bottom flask, the CPs (see Table below) was dissolved in warm degassed water (62.5 mL) followed by the addition of the required amount of degassed acid (see below). The total mixture was degassed for an additional 10 minutes then heated using an oil bath for the required time (see below). At the end of the hydrolysis time, the total mixture was diluted 5-fold with water and then lyophilized to produce the crude product.

| CPs | 6B | 14 | 19F | 23F |
|---|---|---|---|---|
| Amount of CPs | 250 mg in water (62.5 mL) | 250 mg in water (62.5 mL) | 250 mg in water (62.5 mL) | 230 mg in water (62.5 mL) |
| Buffer (mL) | 0.02 M acetic acid (62.5 mL, pH 3.22) | 1 M TFA (62.5 mL) | 0.02 M acetic acid (62.5 mL) | 0.5 M TFA (62.5 mL) |
| Time | 30 h | 7 h | 48 h | 3 h |
| Temperature (° C.) | 100 | 70 | 50 | 70 |
| Crude product (mg) | 200 mg | 260 mg | 200 mg | 250 mg |
| Pure product (mg) | 160 mg | 230 mg | 180 mg | 188 mg |
| M. wt. of product | 2330 | 5200 | 2930 | 4640 |

A gel permeation column (10×1000 mm, Sephadex® -G100) was calibrated with the following molecular weight standards: Dextran standards (M. wt 8800, 39100, 73500, 503,000), glucose (180), sucrose (342) and synthetic PRP hexamer (2340). The purification of oligosaccharides was accomplished using Sephadex® G-100 gel column and oligosaccharides were eluted with Milli-Q water at flow rate of 0.9 mL/min. The fractions were collected every 3 minutes and assayed for the presence of carbohydrates using phenol/sulfuric acid. The fractions containing oligosaccharides with molecular weight 2.5 to 5 kDa were pooled and lyophilized.

Example 4

This Example Describes the Preparation of Oligosaccharides of *N. meningiditis*

As for the acid hydrolysis of pneumococcal CPs, the process as applied to *N. meningitidis* involves acid hydrolysis, lyophilization and purification using gel-filtration chromatography. The conditions for acid hydrolysis of CPs from *N. meningococcal* groups C, W-135 and Y were also optimized. Typically, CPs (10 mg/mL) are mixed with 20 to 80 mM sodium acetate, pH 4.5 to 5.5, in sealed vials under argon at 65° to 100° C. for 8 to 12 hours. Since group B CPs can undergo intramolecular esterification under acidic conditions, hydrolysis was effected under conditions used for CPs group C hydrolysis, but the incubation time was limited to 1 hr and the pH of the reaction was immediately adjusted to pH 7 with 0.1 M NaOH to reverse the esterification process (for details, see Example 1) Group A CPs contain labile phosphodiester bonds, thus they were hydrolyzed under mild acidic condition (such as 10 to 20 mM acetic acid) and incubated at 50° to 100° C. for 30 to 48 hours. At the end of each hydrolysis, the reaction solutions were diluted 5-fold with water and then lyophilized. The crude oligosaccharides were fractioned by Sephadex® G-100 gel filtration chromatography (2×210 cm, see above). Typical chromatographic results are illustrated in FIG. 4. The fractions were assayed for the presence of sialic acid using the resorcinol/sulfuric acid assay (ref. 12). The elution profile was plotted, and chromatographically purified oligosaccharides of 2 to 5 kDa were pooled. Sized oligosaccharides typically contained 6 to 15 repeating units. The yields were 40 to 80%.

Example 5

This Example Describes the Preparation of Multi-valent Oligosaccharides Conjugated Randomly to a Carrier Protein.

To illustrate a potential use of the present invention, *S. pneumoniae* serotypes 6B, 14, 19F and 23F oligosaccharides were randomly and covalently linked to TT as shown in FIG. 1. To a TT solution (8 mg/1.2 mL of PBS), a 4 molar excess of periodate-oxidized 6B (0.5 mg/0.1 mL PBS), 14 (1.4 mg/0.2 mL), 19 F (0.65 mg/0.12 mL) and 23 F (1 mg/0.2 mL) oilgosaccharides were added. The pH of the mixture was adjusted to 7.4 with a few drops of 0.1 M NaOH, and the reaction was stirred for 4 days at 37° C. At day 5, a 10-fold excess (100 μL) of NaCNBH$_3$ (5 mg/mL ) was added to the mixtures and stirred for another 3 days at 37° C. The reaction mixture was then dialysed against excess PBS to remove unreacted oligosaccharides and NaCNBH$_3$ for 3 days at 4° C. The glycoconjugate was purified by the gel-filtration chromatography on a Sephedex G100 column (1.6×100 cm). The elution profile is illustrated in FIG. 5. The glycoconjugate was collected. Protein and carbohydrates analyses were performed and the molar ratio of carbohydrate to protein was found to be 7.1:1. The multiple antigenic glycoconjugate (MAG) was used as an immunogen formulated either with complete Freund's adjuvant or alum. Rabbit and mouse immunogenicity studies were performed. The results are described below.

Example 6

This Example Describes Peptide Synthesis.

Peptides (Table 1) were synthesized using an ABI 430A peptide synthesizer and optimized t-Boc chemistry as described by the manufacturer, then cleaved from the resin by hydrofluoric acid (HF). The peptides were purified by reverse-phase high performance liquid chromatography (RP-HPLC) on a Vydac C4 semi-preparative column (1×30 cm) using a 15 to 55% acetonitrile gradient in 0.1% trifluoryl acetic acid (TFA) developed over 40 minutes at a flow rate of 2 mL/min. All synthetic peptides used in biochemical and immunological studies were >95% pure as judged by analytical HPLC. Amino acid composition analyses performed on a Waters Pico-Tag system were in good agreement with the theoretical compositions. The synthetic MAP was manually prepared using Fmoc solid-phase peptide synthesis chemistry according to a modified method previously described by Tam (ref. 24). A Fmoc-Lys(t-Boc)-TGA resin (500 mg, purchased from BACHEM) with a substitution level of 180 µmol/g was normal by used to prepare MAP. As a general coupling protocol, a 4-fold excess of Fmoc-protected amino acids activated with an equal amount of HBTU and HOBT/DIEA for 1 hr, was used. In order to facilitate the conjugation with oligosaccharides, the substitution level of MAP was reduced to about 50 µmol/g when the first Fmoc-Gly residue was coupled. When the synthesis was completed according to (FIGS. 2A and 2B) a small portion of MAP-resin was cleaved with 95% TFA in the presence of ethane dithiol (EDT) and thioanisol, and amino acid analysis of the cleaved MAP was performed to confirm the amino acid composition.

Example 7

This Example Describes Preparation of Oligosaccharides With Cross-linking Bifunctional Groups.

Attached an amino linker to oligosaccharides. To a periodate-oxidized oligosaccharide solution (3 mg/mL of PBS), a 20 molar excess of 1,4-diaminobutane (10.5 mg) was added. The pH of the mixture was adjusted to 7.4, and then the reaction was stirred for 4 day at 37° C. At day 5, an excess (500 µL) of NaCNBH$_3$ (20 mg/mL) was added to the mixture which was stirred for 3 more days at 37° C. The oligosaccharide derivatized with a functional amino group, was purified by gel-filtration chromatography on a Sephadex® G-50 column (1.6×100 cm).

Attached a thio-directed cross-linker (MBS) to oligosaccharides.

m-Maleimidobenzoyl-N-hydroxysuccinimide (MBS, Pierce) (20 mg; 63.6 mmol) in tetrahydrofuran (1 mL) was added to a solution of amino-derivatized oligosaccharides (4.3 mmol) in 0.1 M phosphate buffer (1 mL), pH 7.5. The reaction mixture was stirred for 30 min at room temperature under argon, then extracted with ether (4×5 mL) to remove excess MBS. The resulting aqueous layer was applied to a Sephadex G-25 column (20×300 mm) equilibrated with 20 mM ammonium bicarbonate buffer, pH 7.2 and eluted with the same buffer. Elution was monitored by absorbance at 280 nm, and the eluted peak was pooled and lyophilized to produce the desired MBS activated oilogsaccharides. The number of maleimide groups incorporated into the oligomers was determined by adding excess 2-mercaptoethanol to the activated oligosaccaharide-MBS and back-titrating the excess using a modified Ellman's method (ref. 25).

Example 8

This Example Describes the Preparation of Linear Glycopeptide Conjugates.

A Fmoc-Gly-Lys(t-Boc)-TGA resin (500 mg) with a substitution level of 50 µmol/g was used to prepare linear peptides containing a T-cell epitope derived from either *S. pneumoniae* or *N. meningiditis* proteins as shown in Table 1. A standard Fmoc chemistry coupling protocol was used (see Example 6). When the synthesis was completed, a small portion of peptide-resin was cleaved with 95% TFA in the presence of EDT and thioanisol to determine the quality of the synthesis. The rest of the peptide-resin was first deprotected at the N-terminal using piperidine, and then washed with dichloromethane, methanol, water, and PBS. The PN(123–140) peptide-resin was mixed with periodate-oxidized *S. pneumoniae* serotype 14 oligosaccharides (1 eq.) in methanol/phosphate buffer (pH 7.8) in the presence of NaCNBH$_3$ at 38° C. for 6 days. After conjugation, the degree of amino groups substitution was determined by the ninhydrine assay and the total sugar content was assayed using the orcinol test. The linear glycopeptide-resin was cleaved with 95% TFA in the presence of EDT and thioanisol. After the work-up, the glycopeptide was assayed for amino acid composition and carbohydrate content.

Example 9

This Example Describes the Preparation of Multivalent MAP Glycopeptide Conjugates.

A MAP resin containing three different T-cell epitopes [PN(123–140), PN(263–281) and SP37, Table 1] derived from *S. pneumoniae* membrane proteins was synthesized using a Fmoc-Gly-Lys-TGA resin with a substitution level of 50 mmol/g as shown in FIGS. 2A and 2B. The whole synthesis was carried out manually using an optimized Fmoc chemistry coupling protocol described above (Example 6). When the synthesis was completed, a small portion of MAP-resin was cleaved with 95% TFA in the presence of EDT and thioanisol. The cleaved MAP was found to have the correct amino acid composition by amino acid analysis. The MAP resin was reduced with DTT to remove the t-butylthio protecting groups from the cysteine residues. After excess washing, the MAP resin was resuspended in a DMF/PBS solution, then mixed with a 4-fold excess of sulfo-SIAB activated oligosaccharides from *S. pneumoniae* serotype 14 (Os14). After overnight mixing at room temperature, the MAP resin was collected by filtration and washed with PBS, DMF and then methanol. The MAP-Os14 resin was subjected to Ellman's test and sulfhydryl group determination. The level of SH substitution was found to be half of the starting value. Recoupling did not increase the amount of Os14 conjugated to the MAP resin. The presence of N-acetylgalactosamine (GlcNAc) in the glyco-MAP resin, a carbohydrate found in Os14, was independently confirmed by carbohydrate analysis. MAP-Os14 was first treated with 1% TFA to remove Mtt (a lysine-protecting group) from Mtt-lysine residues, then neutralized with a mild base, 1% diisopropylethylamine (DIEA)/DMF. The presence of free amino groups was assayed by the ninhydrine test which indicated that >90% of Mtt groups had been removed. The MAP-Os14 resin were resuspended in PBS, and then mixed with 4 equivalent of periodate-oxidized *S. pneumoniae* serotype 6B oligosaccharides (Os6B) in DMF/ phosphate buffer (pH 7.8) in the presence of NaCNBH$_3$ at 38° C. for 6 days. After conjugation, the substitution of amino groups was determined by the ninhydrin assay was found to be 80 to 90% of the original value. Again a double and triple coupling did not improve the conjugation of Os6B to the MAP-Os14 resin. Although the coupling efficiency was poor (about 15%), the presence of ribitol in the MAP conjugate, a carbohydrate found in Os6B, was confirmed by carbohydrate analysis. The MAP-Os14-Os6B conjugate was treated with 20% piperidine in DMF to remove the Fmoc protecting group from Fmoc-lysine residues. After washing, the MAP-Os14-Os-6B resin were mixed with a 4-fold excess of periodate oxidized S. pneumoniae serotype 19F oligosaccharides (Os19F) in DMF/phosphate buffer (pH 7.8) in the presence of NaCNBH$_3$ at 38° C. for 6 days. After conjugation, the degree of amino group substitution measured by the ninhydrin assay was found to be about 90%. The coupling reaction was repeated and its efficiency was determined to be about 15%. However, the presence of N-acetylmannose (ManNAc), a sugar found in Os19F, was detected by carbohydrate analysis. A small portion of MAP glycoconjugate-resin was cleaved with 95% TFA in the presence of EDT and thioanisol. After the work-up, the MAP-glycoconjugate was assayed for amino acid composition and carbohydrate content, and found to have a correct amino acid composition and a correct carbohydrate content. Although the overall yield was very low (about 5%), these results nevertheless demonstrate that different oligosaccharides can be selectively and sequentially conjugated to a MAP resin.

Example 10

This Example Describes the Preparation of Native Polysaccharide-polylysine Conjugate.

A 0.5 mL of periodate-oxidized polysaccharides (25 mg in 1 mL of 0.1 M sodium phosphate buffer, pH 6.0), prepared from native S. pneumoniae or N. meningiditis polysaccharides treated with aqueous sodium periodate, was added to polylysine (5 mg) in 2 mL of 0.2 M sodium phosphate buffer, pH 8.0, followed by the addition of sodium cyanoborohydride (10 eqv. to polylysine). After incubation at 37° C. for 5 days, the reaction mixture was dialysed against 0.1 M phosphate buffer (4×1 L), pH 7.5, and the resulting solution was applied onto an analytical Superose 12 column (15×300 mm, Pharmacia) equilibrated with 0.2 M sodium phosphate buffer, pH 7.2, and eluted with the same buffer. Fractions were monitored for absorbance at 230 nm. The major peak was pooled. The amount of protein was determined using the Bio Rad protein assay. The presence of polysaccharides was confirmed by the orcinol test.

Example 11

This Example Describes Mouse Immunogenicity Studies of Multivalent Oligosaccharides-TT Conjugates.

Five mice (BALB/c) were immunized intramuscularly (im) with multivalent oligosaccharide-TT conjugates (20 µg of oligosaccharides) emulsified in Freund's complete adjuvant (FCA), and followed by two booster doses (half amount of the same immunogen in incomplete Freund's adjuvant) at 2 week intervals. Antisera were collected, inactivated at 56° C., and then stored at −20° C.

Example 12

This Example Describes Rabbit Immunogenicity Studies of Multivalent Oligosaccharides-TT Conjugates Formulated in Alum.

Rabbits were immunized intramuscularly with 0.5 mL of multivalent oligosaccharides-TT conjugates (20 µg oligosaccharides equivalent) mixed with 3 mg AlPO$_4$ per mL, followed by two booster doses (half amount of the same immunogen) at 2 week intervals. Antisera were collected every 2 weeks after the first injection, heat-inactivated at 56° C. for 30 min and stored at −20° C.

Example 13

This Example Describes Rabbit Immunogenicity Studies of Multivalent Oligosaccharides-carriers Conjugates Formulated in FCA.

Rabbits were immunized intramuscularly with 0.5 mL of multivalent oligosaccharides-TT or oligosaccharides-MAP conjugates (conjugates containing 12 µg oligosaccharides equivalent mixed with 1 mL of FCA), followed by two booster doses (half amount of the same immunogen formulated with Fruend's incomplete adjuvant (IFA)) at 2 week intervals. Antisera were collected every 2 weeks after the first injection, heat-inactivated at 56° C. for 30 min and stored at −20° C.

Example 14

This Example Describes Peptide-specific ELISAs

Microtiter plate wells (Nunc-Immunoplate, Nunc, Denmark) were coated with 500 ng of individual peptides in 50 µL of coating buffer (15 mM Na$_2$CO$_3$, 35 mM NaHCO$_3$, pH 9.6) for 16 hr at room temperature. The plates were then blocked with 0.1% (w/v) BSA in phosphate buffer saline (PBS) for 30 min at room temperature. Serially diluted antisera were added to the wells and incubated for 1 hr at room temperature. After removal of the antisera, the plates were washed five times with PBS containing 0.1% (w/v) Tween-20 and 0.1% (w/v) BSA. F(ab')$_2$ from goat anti-rabbit IgG antibodies conjugated to horseradish peroxidase (Jackson ImmunoResearch Labs Inc., Pa.) were diluted (1/8,000) with washing buffer, and added onto the microtiter plates. After 1 hr incubation at room temperature, the plates were washed five times with the washing buffer. The plates were then developed using tetramethylbenzidine (TMB) in H$_2$O$_2$ (ADI, Toronto) as substrate. The reaction was stopped with 1N H$_2$SO$_4$ and the optical density was measured at 450 nm using a Titretek Multiskan II (Flow Labs., Virginia). Two irrelevant pertussis toxin peptides NAD-S1 (19 residues) and S3(123–154) (32 residues) were included as negative controls in the peptide-specific ELISAs. Assays were performed in triplicates, and the reactive titre of an antiserum was defined as the dilution consistently showing a two-fold increase in absorbance value over that obtained with the pre-immune serum.

Example 15

This Example Describes Anti-polysaccharide Antibody Measurement.

Microtiter plate wells (Nunc-Immunoplate, Nunc, Denmark) were coated with 200 ng of S. pneumoniae or N. meningiditis polysaccahrides-polylysine conjugates in 200 µL of coating buffer (15 mM Na$_2$CO$_3$, 35 mM NaHCO$_3$, pH 9.6) for 16 hr at room temperature. The plates were then blocked with 0.1% (w/v) BSA in phosphate buffer saline (PBS) for 30 min at room temperature. Serially diluted antisera raised against PRP-carrier conjugates were added to the wells and incubated for 1 hr at room temperature. After removal of the antisera, the plates were washed five times with PBS containing 0.1% (w/v) Tween-20 and 0.1% (w/v)

BSA. F(ab')₂ from goat anti-rabbit IgG or anti-mouse IgG antibodies conjugated to horseradish peroxidase (Jackson ImmunoResearch Labs Inc., Pa.) were diluted (1/8,000) with washing buffer, and added onto the microtiter plates. After 1 hr incubation at room temperature, the plates were washed five times with the washing buffer. The plates were then developed using the substrate tetramethylbenzidine (TMB) in $H_2O_2$ (ADI, Toronto), the reaction was stopped with 1N $H_2SO_4$ and the optical density was measured at 450 nm using a Titretek Multiskan II (Flow Labs., Virginia). Assays were performed in triplicates, and the reactive titre of an antiserum was defined as the dilution consistently showing a two-fold increase in O.D. value over that obtained with the pre-immune serum.

Example 16

This Example Describes a Proliferation Assay for Synthetic T-cell Epitopes.

T-cell epitope mapping was performed by priming BALB/c mice with 5 μg of individual carrier proteins. Three weeks later, the spleens were removed and the splenocytes cultured in RPMI 1640 (Flow Lab) supplemented with 10% heat-inactivated fetal calf serum (Gibco), 2 mM L-glutamine (Flow Lab), 100 U/mL penicillin (Flow Lab), 100 μg/mL streptomycin (Flow Lab), 10 unit/mL rIL-2 and 50 μM 2-mercaptoethanol (sigma) for 5–7 days. Proliferative responses of the primed splenocytes to the panel of peptides were determined in a standard in vitro assay (ref. 26). Briefly, $10^6$ splenocytes were co-cultured in a 96-well microtiter plate with $5 \times 10^5$ irradiated (1700 Rad) fresh syngeneic spleen cells used as source of antigen presenting cells (APC) in the presence of increasing molar concentrations (0.03 to 3 μM of peptide dissolved in the culture medium without IL-2). Cultures were kept for 40 hr in a humidified 5% $CO_2$/air incubator maintained at 37° C. During the final 16 hr of culture, 0.5 μCi of [³H]-Tdr (5 Ci/mmol, NEN) was added to each wells. The cells were then harvested onto glass fibre filters, and the incorporation of ³H-thymidine into cellular DNA was measured in a scintillation β-counter (Beckman). Results are expressed as the mean of triplicate determinations performed for each peptide concentration. The standard deviation was always <15%. Proliferative responses were considered as positive when ³H-thymidine incorporation was three-fold above that obtained with either irrelevant peptides or the culture medium.

SUMMARY OF THE DISCLOSURE

In summary of this disclosure, the present invention provides certain novel multivalent immunogenic oligosaccharides as well as novel conjugation procedures in their preparation, their use as vaccines and their use in the provision of antibodies for diagnostic use. Modifications are possible within the scope of this invention.

TABLE 1

POTENTIAL T-CELL EPITOPES FROM MENINGOCOCCAL AND PNEUMOCOCCAL PROTEINS

| PEP-TIDES | SEQUENCE | COMMENTS | SEQ ID NO: |
|---|---|---|---|
| NMTB-P2 | PFTISDSDSLEGGFYGPKGEEL-AGKFLSNNDKVAAVFG | Bactericidal Epitope | 1 |
| NM-C1-1 | KAKSRIRTKISDFGSFIGFKGSE-DLGEGLKA | Human T-cell epitope | 2 |

TABLE 1-continued

POTENTIAL T-CELL EPITOPES FROM MENINGOCOCCAL AND PNEUMOCOCCAL PROTEINS

| PEP-TIDES | SEQUENCE | COMMENTS | SEQ ID NO: |
|---|---|---|---|
| NM-C1-2 | VPAQNSKSAYKPAYYTKDTNNN-LTLVPAVVGK | Human T-cell epitope | 3 |
| NM-Pi-1 | AEQKSAVTEYYLNHGEWPGNN-TSAGVASSSTIKGKYVKEV | Adhesion Epitopes | 4 |
| PN (123–140) | GVRGAVNDLLAKWHQDYGQG | Pneumolysin (123–40) | 5 |
| PN-(263–281) | GFEALIKGVKVAPQTEWKQIG | Pneumolysin (263–81) | 6 |
| SP37 | GIIYAKNIAKQLIAKDPKNKDF-YEKNG | 37kDa Protein (1–30) | 7 |
| PSP-AA | IKEIDESESEDYAKEGFRAPLQSK-IDAKKAKLSKLEELSDKIDELDA-EIAKLEDQIKAAEENNNVEDY-EKEG (C) | Protective Epitope of PspA (193–261) | 8 |

TABLE 2

Anti-peptide antibody responses in rabbits immunized with combined linear glycopeptide conjugates [6B-PN(123–140) + 14-PN(263–281) + 23F-PN(123–140)]

| | Anti-peptide antibody titer[a] | |
|---|---|---|
| Peptides titre[b] | Pre-Immune | Geometric mean |
| PN(123–140) | <100 | 12,800 |
| PN(263–281) | <100 | 3,200 |

[a]Total anti-peptide antibody responses were determined by peptide-specific ELISAs.
[b]Antisera were obtained from rabbits immunized.

TABLE 3

Anti-peptide antibody responses in rabbits immunized with a MAP glycopeptide conjugates.

| | Anti-peptide antibody titer[a] | |
|---|---|---|
| Peptides titre[b] | Pre-Immune | Geometric mean |
| PN (123–140) | <100 | 633,400 |
| PN (263–281) | <100 | 12,800 |
| SP37 | <100 | 51,200 |

[a]Total anti-peptide antibody responses were determined by peptide-specific ELISAs.
[b]Antisera were obtained from rabbits immunized three times with the MAP glycopeptide conjugate.

REFERENCES

1. MMWR, (1994) 43:23–26
2. MMWR (1989) 38:64–76
3. Austrian R. (1981) *Rev. Infect. Dis.* 3 (Suppl):S1–S17
4. Dagan et al., (1992) *J. Am. Med. Assoc.* 268:3328–3332)
5. H. Jennings et al, (1986), *J. Immun.* 127, 1011
6. H. Jennings et al. (*J. Immunol.,* 1986, 137, 1708
7. Peeters et al., (1991) *Infect. Immun.* 59:3504–3510
8. Paradiso et al., (1993) *Vaccine Res.* 4:239–248
9. Schneerson et al. (1980) *J. expt. Med.* 152: 361
10. Barington et al. 1993, *Infect. Immun.* 61:432–438
12. Svennerholm, 1957, *Biochem. Biophys. Acta.* 604:24
13. Walker et al. (1987), *Infect. Immun.* 58:1184–1189

14. Yother and Briles (1992), *J. Bacteriol.* 174:601–609
15. Sampson et al., (1994), *Infect. Immun.* 62:319–324
16. Rokbi et al., (1995) *FEMS Microbiol. Lett.* 132:277–283
17. Stimson et al., (1995), *Mol. Microbiol.* 17:1201–1214
18. McGuinness et al., (1990), *J. Exp. Med.* 171:1871–1882
19. Wiertz et al., In Rivier, J and Marshall, G. R. (Ed.) *Peptides: Chemistry, Structure and Biology*, (Proceedings of the 11th American Peptide Symposium), ESCOM, Leiden, 1990, p.371–372
20. De Velasco et al., (1995), *Infect. Immun.* 63:961–968
21. McQueen et al., (1991) *Pediatr. Res.* 31 (part 2):Abstract 1056;
22. Eby et al., (1994) In Vaccine 94:*Modern Approaches to Vaccines* pp. 119–124. Edited by E. Norry, F. Brown, R. M. Chanock and Ginsberg, H. S. Cold Spring Harbor, N.Y. Cold Spring Harbor Press
23. Kandil et al., (1997) *Glycoconjugate J.* 14:13–17
24. Tam (1996, *J. Immun. Meth.* 196:1732)
25. Ridles et al., (1983) *Methods Enzymol.* 91: 49–60).
26. Sia et al, (1987), *Scan. J. Immunol.* 26: 683–690

What we claim is:

1. A multivalent immunogenic molecule, comprising:
   a carrier molecule containing at least one T-cell epitope, said carrier molecule comprising a multiple antigen peptide having a plurality of carrier peptide segments linked to each other through lysine groups in a dendritic structure, and
   at least two different bacterial capsular oligosaccharide fragments each from a different serotype, each said different bacterial capsular oligosaccharide fragment being linked by site directed glycoconjugation to a different one of said plurality of carrier peptide segments and each said different bacterial capsular oligosaccharide fragment containing at least one functional B-cell epitope, wherein said carrier molecule imparts enhanced immunogenicity to said at least two oligosaccharide fragments.

2. The molecule of claim 1 wherein said capsular oligosaccharide fragments are capsular oligosaccharide fragments of *Streptococcus pneumoniae*.

3. The molecule of claim 2 wherein said capsular oligosaccharide fragments are derived from at least two capsular polysaccharides of *S. pneumoniae* serotypes 1, 4, 5, 6B, 9V, 14, 18C, 19F and 23F.

4. The molecule of claim 3 wherein each of the carrier peptide segments of said carrier molecule is a T-cell epitope-containing peptide fragment of *S. pneumoniae*.

5. The molecule of claim 1 wherein said capsular oligosaccharide fragments are capsular polysaccharide fragments of *Neisseria meningitidis*.

6. The molecule of claim 5 wherein said oligosaccharide fragments are derived from at least two capsular polysaccharides of *N. meningitidis* Group A, B, C, W-135 and Y.

7. The molecule of claim 6 wherein each of the carrier peptide segments of said carrier molecule is a T-cell epitope-containing protein fragment of *N. meningitidis*.

8. The multivalent immunogenic molecule of claim 1 wherein said oligosaccharide fragments are sized from about 2 to about 5 kDa.

9. An immunogenic composition for meningitis, comprising:
 (1) a multiple glycoconjugate according to claim 2,
 (2) a multiple glycoconjugate according to claim 5, and
 (3) an immunogenic synthetic PRP-peptide conjugate.

10. The immunogenic composition of claim 9 further comprising at least one additional antigen.

11. The immunogenic composition of claim 9 wherein said multiple glycoconjugate according to claim 2 is derived from at least two capsular polysaccharides of *S. pneumoniae* serotypes 1, 4, 5, 6B, 9V, 14, 18C, 19F and 23F and said multiple conjugate according to claim 5 is derived from at least two capsular polysaccharides of *Neisseria meningitidis* serotypes A, B, C, Y and W.

12. A diagnostic kit for determining the presence of a multivalent immunogenic molecule of claim 1 comprising:
 (a) the multivalent immunogenic molecule;
 (b) means for contacting the multivalent molecule with the sample to produce complexes comprising the multivalent molecule and any said antibodies present in the sample; and
 (c) means for determining production of the complexes.

13. The kit of claim 12 wherein said immunogenic molecule of claim 1 is present in the form of the immunogenic composition of claim 9.

14. A diagnostic kit for determining the presence of a multivalent immunogenic molecule in a sample, comprising:
 (a) antibodies specific for carbohydrate fragments of the multivalent immunogenic molecule;
 (b) means for contacting the antibodies with the sample to produce a complex comprising multivalent immunogenic molecule and the antibodies; and
 (c) means for determining the production of the complex.

15. The kit of claim 14 wherein said antibodies are antibodies to the components of the immunogenic composition of claim 9.

* * * * *

SEQUENCE LISTING

<160> NUMBER OF SEQ ID NOS: 8

<210> SEQ ID NO 1
<211> LENGTH: 38
<212> TYPE: PRT
<213> ORGANISM: Neisseria meningitidis

<400> SEQUENCE: 1

Pro Phe Thr Ile Ser Asp Ser Asp Ser Leu Glu Gly Gly Phe Tyr Gly
 1               5                  10                  15

Pro Lys Gly Glu Glu Leu Ala Gly Lys Phe Leu Ser Asn Asn Asp Lys
            20                  25                  30

Val Ala Ala Val Phe Gly
        35

<210> SEQ ID NO 2
<211> LENGTH: 31
<212> TYPE: PRT
<213> ORGANISM: Neisseria meningitidis

<400> SEQUENCE: 2

Lys Ala Lys Ser Arg Ile Arg Thr Lys Ile Ser Asp Phe Gly Ser Phe
 1               5                  10                  15

Ile Gly Phe Lys Gly Ser Glu Asp Leu Gly Glu Gly Leu Lys Ala
            20                  25                  30

<210> SEQ ID NO 3
<211> LENGTH: 32
<212> TYPE: PRT
<213> ORGANISM: Neisseria meningitidis

<400> SEQUENCE: 3

Val Pro Ala Gln Asn Ser Lys Ser Ala Tyr Lys Pro Ala Tyr Tyr Thr
 1               5                  10                  15

Lys Asp Thr Asn Asn Asn Leu Thr Leu Val Pro Ala Val Val Gly Lys
            20                  25                  30

<210> SEQ ID NO 4
<211> LENGTH: 40
<212> TYPE: PRT
<213> ORGANISM: Neisseria meningitidis

<400> SEQUENCE: 4

Ala Glu Gln Lys Ser Ala Val Thr Glu Tyr Tyr Leu Asn His Gly Glu
 1               5                  10                  15

Trp Pro Gly Asn Asn Thr Ser Ala Gly Val Ala Ser Ser Ser Thr Ile
            20                  25                  30

Lys Gly Lys Tyr Val Lys Glu Val
        35                  40

```
<210> SEQ ID NO 5
<211> LENGTH: 20
<212> TYPE: PRT
<213> ORGANISM: Streptococcus pneumoniae

<400> SEQUENCE: 5

Gly Val Arg Gly Ala Val Asn Asp Leu Leu Ala Lys Trp His Gln Asp
 1               5                  10                  15

Tyr Gly Gln Gly
            20

<210> SEQ ID NO 6
<211> LENGTH: 21
<212> TYPE: PRT
<213> ORGANISM: Streptococcus pneumoniae

<400> SEQUENCE: 6

Gly Phe Glu Ala Leu Ile Lys Gly Val Lys Val Ala Pro Gln Thr Glu
 1               5                  10                  15

Trp Lys Gln Ile Gly
            20

<210> SEQ ID NO 7
<211> LENGTH: 27
<212> TYPE: PRT
<213> ORGANISM: Streptococcus pneumoniae

<400> SEQUENCE: 7

Gly Ile Ile Tyr Ala Lys Asn Ile Ala Lys Gln Leu Ile Ala Lys Asp
 1               5                  10                  15

Pro Lys Asn Lys Asp Phe Tyr Glu Lys Asn Gly
            20                  25

<210> SEQ ID NO 8
<211> LENGTH: 73
<212> TYPE: PRT
<213> ORGANISM: Streptococcus pneumoniae

<400> SEQUENCE: 8

Ile Lys Glu Ile Asp Glu Ser Glu Ser Glu Asp Tyr Ala Lys Glu Gly
 1               5                  10                  15

Phe Arg Ala Pro Leu Gln Ser Lys Ile Asp Ala Lys Lys Ala Lys Leu
                20                  25                  30

Ser Lys Leu Glu Glu Leu Ser Asp Lys Ile Asp Glu Leu Asp Ala Glu
            35                  40                  45

Ile Ala Lys Leu Glu Asp Gln Ile Lys Ala Ala Glu Glu Asn Asn Asn
        50                  55                  60

Val Glu Asp Tyr Phe Lys Glu Gly Cys
65                  70
```